US009572950B2

(12) United States Patent
Power et al.

(10) Patent No.: US 9,572,950 B2
(45) Date of Patent: Feb. 21, 2017

(54) SUPPLEMENTAL OXYGEN DELIVERY SYSTEM

(71) Applicant: STAMFORD DEVICES LIMITED, Dangan, Galway (IE)

(72) Inventors: John Sylvester Power, Moycullen (IE); James B. Fink, San Mateo, CA (US); Conor Paul Duffy, Roscahill (IE); Trevor Stephen Fahy, Galway (IE)

(73) Assignee: Stamford Devices Limited, Galway (IE)

( * ) Notice: Subject to any disclaimer, the term of this patent is extended or adjusted under 35 U.S.C. 154(b) by 410 days.

(21) Appl. No.: 13/829,044

(22) Filed: Mar. 14, 2013

(65) Prior Publication Data

US 2013/0199529 A1  Aug. 8, 2013

Related U.S. Application Data

(63) Continuation of application No. 12/568,399, filed on Sep. 28, 2009, now Pat. No. 8,418,690.

(Continued)

(51) Int. Cl.
*A61M 11/00* (2006.01)
*A61M 16/16* (2006.01)
(Continued)

(52) U.S. Cl.
CPC .......... *A61M 16/16* (2013.01); *A61M 11/002* (2014.02); *A61M 11/003* (2014.02);
(Continued)

(58) Field of Classification Search
CPC  A61M 15/001; A61M 15/00; A61M 15/0005; A61M 15/0085; A61M 15/0086; A61M 16/00; A61M 15/08; A61M 16/16; A61M 11/005; A61M 11/002; A61M 16/0672; A61M 11/003; A61M 16/0875; A61M 16/0057; A61M 16/0666; A61M 16/14; A61M 2202/0208; A61M 2206/01
(Continued)

(56) References Cited

U.S. PATENT DOCUMENTS 3,404,843 A  10/1968 Szekely
5,164,740 A  11/1992 Ivri
(Continued)

FOREIGN PATENT DOCUMENTS

JP  61238247  10/1986
JP  2003-514660  4/2003
(Continued)

OTHER PUBLICATIONS

International Search Report for PCT/IE2009/000067, dated Jan. 4, 2010, published as WO 2010/035251.

*Primary Examiner* — Steven Douglas
(74) *Attorney, Agent, or Firm* — Bookoff McAndrews, PLLC

(57) ABSTRACT

A supplemental oxygen delivery system is described in which Aerosol is delivered into a housing which sits in the circuit from the supplemental oxygen supply and optional humidifier. The supplemental oxygen passes through this chamber in which the aerosol is located, and collects the aerosol transporting it to a patient via a nasal cannula or a face mask. An aerosol generator is mounted to the housing and delivers aerosol into an oxygen stream flowing between an inlet and an outlet of the housing. The housing also has a removable plug in the base thereof for draining any liquid that accumulates in the housing. There is no disruption of oxygen delivery to patients using nasal cannulas who currently have to use a separate face-mask when receiving nebulized medication.

18 Claims, 29 Drawing Sheets

Related U.S. Application Data

(60) Provisional application No. 61/100,491, filed on Sep. 26, 2008.

(51) Int. Cl.
| | | |
|---|---|---|
| *A61M 15/00* | (2006.01) | |
| *A61M 16/14* | (2006.01) | |
| *A61M 16/00* | (2006.01) | |
| *A61M 16/06* | (2006.01) | |
| *A61M 16/08* | (2006.01) | |
| *B05B 12/08* | (2006.01) | |
| *B05B 17/00* | (2006.01) | |
| *B05B 17/06* | (2006.01) | |

(52) U.S. Cl.
CPC ...... *A61M 11/005* (2013.01); *A61M 15/0085* (2013.01); *A61M 16/0057* (2013.01); *A61M 16/0666* (2013.01); *A61M 16/0672* (2014.02); *A61M 16/0875* (2013.01); *A61M 16/14* (2013.01); *A61M 2202/0208* (2013.01); *A61M 2206/14* (2013.01); *B05B 12/081* (2013.01); *B05B 17/0646* (2013.01); *B05B 17/0669* (2013.01)

(58) Field of Classification Search
USPC .......... 128/203.15, 200.18, 200.14, 200.21,128/205.24, 203.12, 204.18, 204.21; 514/34, 514/37, 39, 41; 239/332, 338
See application file for complete search history.

(56) References Cited

U.S. PATENT DOCUMENTS

| | | |
|---|---|---|
| 5,186,166 A | 2/1993 | Riggs |
| 5,355,872 A | 10/1994 | Riggs et al. |
| 5,586,550 A | 12/1996 | Ivri et al. |
| 5,758,637 A | 6/1998 | Ivri et al. |
| 5,797,389 A | 8/1998 | Ryder |
| 5,938,117 A | 8/1999 | Ivri |
| 6,044,841 A | 4/2000 | Verdun et al. |
| 6,085,740 A * | 7/2000 | Ivri ................. A61M 11/005 128/200.14 |
| 6,540,154 B1 | 4/2003 | Ivri et al. |
| 6,546,927 B2 | 4/2003 | Litherland et al. |
| 6,755,189 B2 | 6/2004 | Ivri et al. |
| 6,926,208 B2 | 8/2005 | Ivri |
| 7,174,888 B2 | 2/2007 | Ivri et al. |
| 8,196,573 B2 | 6/2012 | Fink et al. |
| 2003/0205229 A1 | 11/2003 | Crockford et al. |
| 2005/0011514 A1 | 1/2005 | Power et al. |
| 2005/0217666 A1 | 10/2005 | Fink et al. |
| 2007/0267010 A1 | 11/2007 | Fink et al. |
| 2009/0288658 A1* | 11/2009 | Charan ............... A61K 9/0078 128/200.14 |
| 2009/0308384 A1 | 12/2009 | Power et al. |
| 2012/0251594 A1* | 10/2012 | Longest ............... A61K 9/008 424/400 |

FOREIGN PATENT DOCUMENTS

| | | |
|---|---|---|
| JP | 2008-536546 | 9/2008 |
| JP | 5008093 | 8/2012 |
| WO | WO-2008/089195 | 7/2008 |

\* cited by examiner

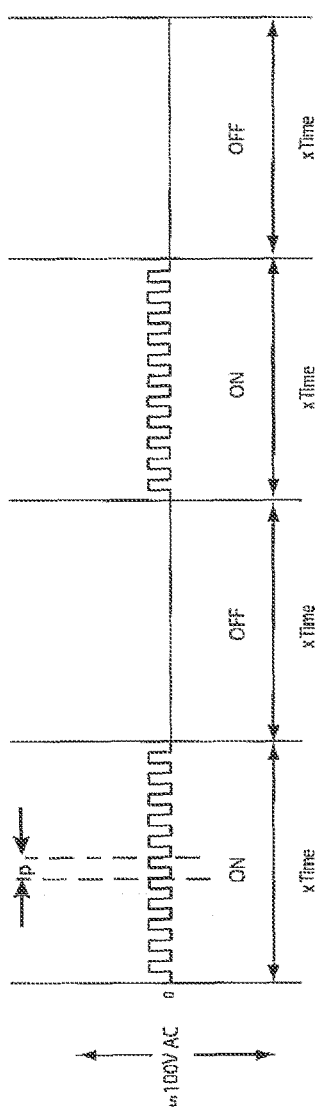
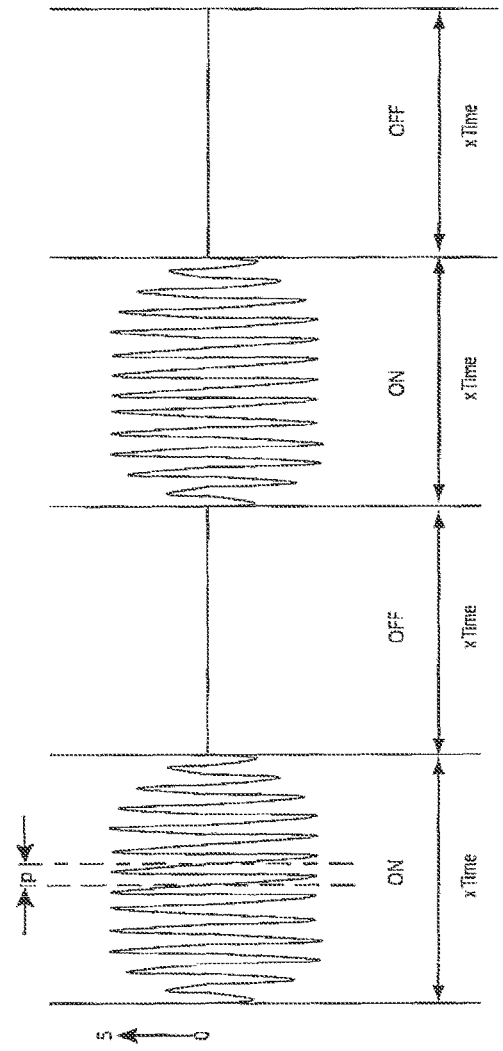
Fig. 26(a)
Fig. 26(b)

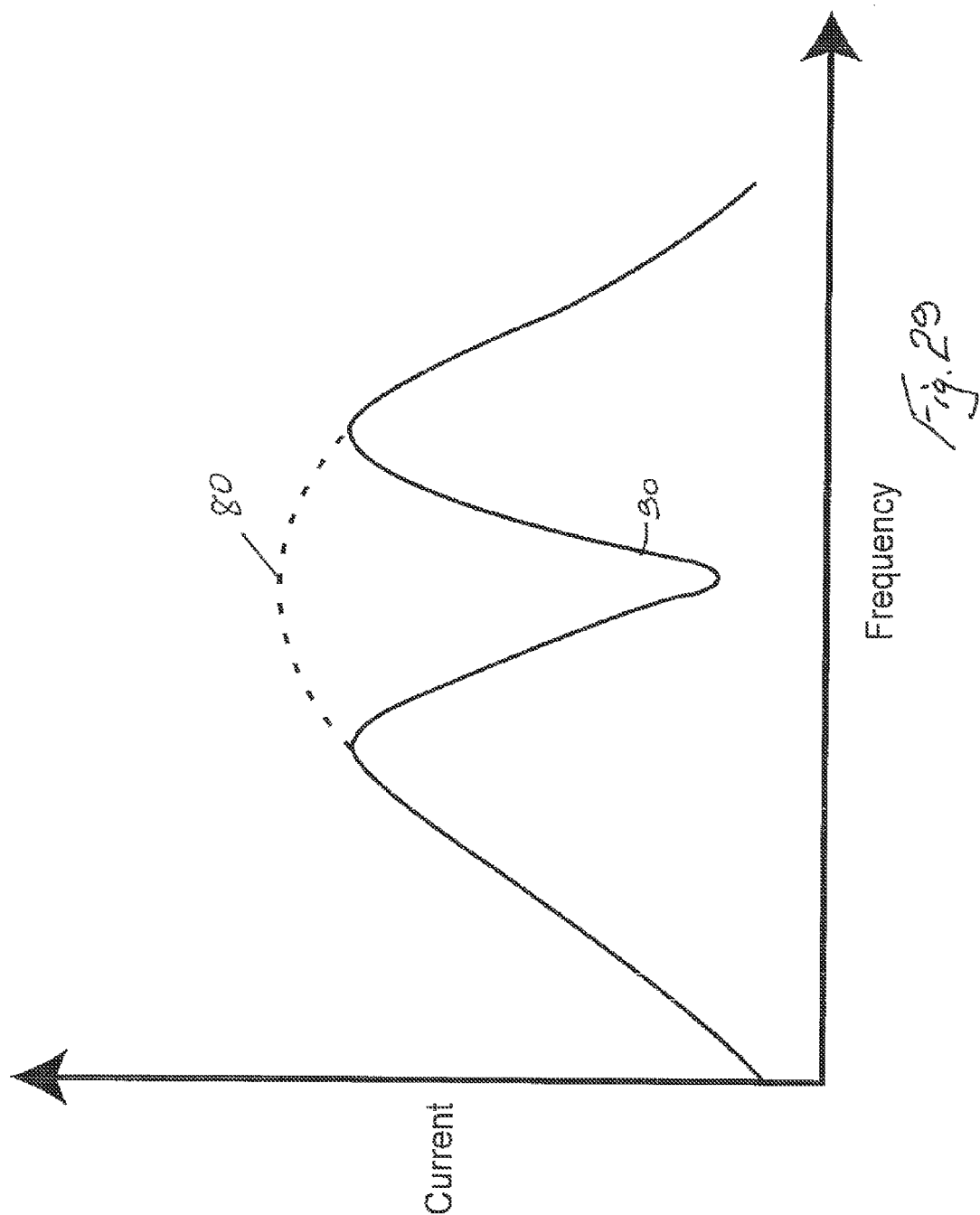

SUPPLEMENTAL OXYGEN DELIVERY SYSTEM

The present application is a continuation of U.S. patent application No. 12/568,399, filed Sep. 28, 2009, the complete contents of which are incorporated herein by reference, and which claims the benefit of U.S. Provisional Application No. 61/100,491, filed Sep. 26, 2008, the complete contents of which are Incorporated herein by reference.

INTRODUCTION

The invention relates to a system for delivery of supplemental oxygen to a patient. In particular, the invention relates to a nasal cannula system For patients undergoing mechanical ventilation, aerosol delivery is a well established therapy. Aerosol is added to the humidified inspiratory gas by placing a T-piece or equivalent in the circuit and entraining the aerosol with the humidified inspiratory gas. In such arrangements the aerosolisation device is downstream of the humidifier and upstream of the patient.

Continuous flow non-invasive therapy is also known in which a patient continues to breathe room air but is supplied with a continuous flow of supplemental oxygen delivered via nasal cannula or to a mask via narrow bore tubing. There are two different types of system. The first is generally referred to as high flow therapy where the flow requires additional heating or humidity to ensure patient comfort. The second is supplemental oxygen therapy where flow rates are low and oxygen is generally supplied direct from a wall supply or a gas bottle supply. This latter system is a low cost simplified therapy that does not usually carry the burden of high cost gas conditioning systems such as controlled heated humidification equipment.

At present, patients undergoing supplemental oxygen therapy delivered via a nasal cannula must be taken off the cannula and must use a separate facemask or mouthpiece for nebuliser treatment.

STATEMENTS OF INVENTION

According to the invention there is provided a supplemental oxygen delivery system for delivery of supplemental oxygen from an oxygen supply to a patient, the system comprising a delivery tube for delivery of supplemental oxygen from a supply to a patient; and an aerosol generator for delivery of aerosol into the delivery tube.

In one embodiment the system comprises a housing through which supplemental oxygen is led, the chamber having an inlet and an outlet.

The housing may be adapted to retain larger aerosol particles within the housing.

In one embodiment the volumetric mean diameter of particles at the outlet of the housing is less than the volumetric mean diameter of particles generated by the aerosol generator.

The volumetric mean diameter of the aerosol particles at the outlet of the housing may be less than 4.5 microns, less than 4 microns, less than 3.5 microns, approximately 3 microns.

In one aspect the housing comprises means to encourage localised deposition of larger aerosol particles.

The housing may comprise an internal wall to retard the flow of larger aerosol particles. The internal wall may be located between the housing inlet and the housing outlet. In one case the internal wall extends below the level of the housing inlet.

In one embodiment the internal wall comprises a screen to retard the flow or larger particles.

In one case the internal wall defines a baffle.

In one embodiment the housing comprises a screen to retard larger aerosol particles. The screen may be provided by a perforated internal divider. Alternatively, the screen is provided adjacent to the outlet from the housing.

In one embodiment the housing inlet is located below the level of the housing outlet. Alternatively, the housing inlet is located substantially at the same level as that of the housing outlet.

In one embodiment the housing comprises a chamber for collection of droplets.

The housing may comprise a drain port.

In one case the housing comprises a fluid reservoir for humidification of supplemental oxygen. The housing may comprise means for directing supplemental oxygen to travel through the fluid reservoir.

In one embodiment the aerosol generator is mounted to the housing for delivery of aerosol into the housing.

The aerosol generator may comprise an aerosol outlet which is located in the housing intermediate the housing inlet and the housing outlet.

In one aspect the delivery system comprises a humidifier for humidifying supplemental oxygen.

In this case the aerosol generator may be mounted to the humidifier for delivery of aerosol into humidified supplemental oxygen. The housing may be located downstream of the humidifier.

In one embodiment the supplemental oxygen delivery tube has a diameter of from 2 mm to 5 mm.

In one embodiment the flow of supplemental oxygen is less than about 3 liters per minute.

In one case the delivery system comprises a nasal cannula.

In another case the delivery system comprises a face mask.

The aerosol generator may comprise a vibratable member having a plurality of apertures extending between a first surface and a second surface thereof.

The first surface may be adapted to receive fluid to be aerosolised.

The aerosol generator may be configured to generate an aerosol at the second surface.

The vibratable member may be dome-shaped in geometry.

In one case the vibratable member comprises a piezoelectric clement.

The system may comprise a controller for controlling the operation of the aerosol generator.

The aerosol may contain a therapeutic and/or prophylactic agent. According to the invention there is provided a non-invasive positive pressure ventilation system, especially a nasal cannula system comprising an aerosol generator for introducing an aerosol into gas passing through the non-invasive ventilation system such as a nasal cannula system.

In one embodiment the nasal cannula system comprises a humidifier.

In one case the aerosol generator may be adapted to deliver aerosol into gas passing through the humidifier. The aerosol generator may comprise an outlet through which aerosol is delivered and the outlet is located in the humidifier. In one case the humidifier is a bubble humidifier.

In another case the aerosol generator is located downstream of the humidifier.

In one embodiment the nasal cannula system comprises a housing through which the gas is passed, the aerosol generator comprising an outlet through which aerosol is delivered and the outlet is located in the housing. The housing may comprise a gas inlet and a gas outlet and the aerosol generator outlet is located to deliver aerosol into the gas as it passes through the housing.

In one case the housing comprises a chamber for collection of droplets. The chamber may comprise a droplet drainage port.

In one case the aerosol generator itself provides a humidifier.

In one embodiment the aerosol generator comprises a vibratable member having a plurality of apertures extending between a first surface and a second surface thereof The first surface may be adapted to receive fluid to be aerosolised. The aerosol generator may be configured to generate an aerosol at the second surface.

In one case the vibratable member is dome-shaped in geometry.

The vibratable member may comprise a piezoelectric element.

In one case the apertures in the vibratable member are sized to aerosolise fluid by ejecting droplets of the water such that the majority of the droplets by mass have a size of less than 5 micrometers.

The apertures in the vibratable member may be sized to aerosolise fluid by ejecting droplets of the water such that the majority of the droplets by mass have a size of less than 3 micrometers.

The system in one case comprises a controller for controlling the operation of the aerosol generator. The controller may be configured to control the pulse rate at a set frequency of vibration of the vibratable member. The controller may be impedance matched to the aerosol generator.

In one embodiment the system comprises means to determine whether fluid is in contact with the aerosol generator. The determining means may be configured to determine at least one electrical characteristic of the aerosol generator. The determining means may be configured to determine at least one electrical characteristic of the aerosol generator over a range of vibration frequencies.

In one case the determining means is configured to compare the at least one electrical characteristic against a pre-defined set of data.

While the invention is described with reference to a nasal cannula system it may be applied to any suitable non-invasive positive pressure breathing assistance system including a face mask system.

BRIEF DESCRIPTION OF THE DRAWINGS

The invention will be more clearly understood from the following description thereof given by way of example only with reference to the accompanying drawings, in which:

FIGS. 26(a) and 26(b) are graphs of DC voltage versus time and AC voltage versus time respectively to achieve a 50% aerosol output-FIG. 26(a) illustrates the waveform output from a microprocessor to a drive circuit and FIG. 26(b) illustrates the waveform output from a drive circuit to a nebuliser;

-FIG. 27(a) illustrates the waveform output from a microprocessor to a drive circuit and FIG. 27(b) illustrates the waveform output from a drive circuit to a nebuliser;

FIG. 29 is a graph of frequency versus current for another apparatus according to the invention.

DETAILED DESCRIPTION

Figure 1:
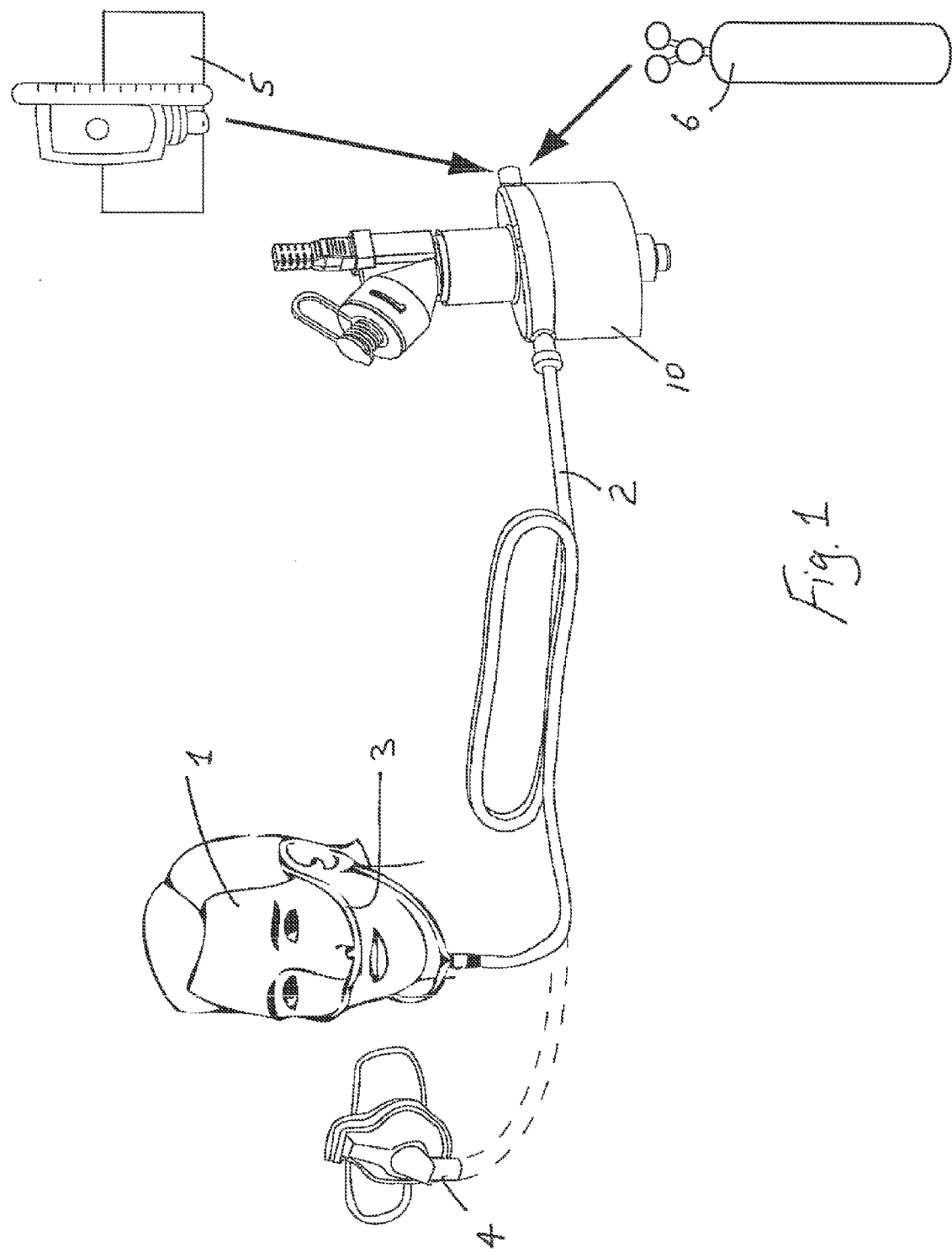
FIG. 1 is a diagram of a nasal cannula system according to an embodiment of the invention.

Referring initially to FIG. 1 there is illustrated a cannula system according to the invention in which patient 1 undergoing supplemental oxygen therapy is supplied with gas through narrow bore tubing 2 to a nasal cannula 3 or to an oxygen face mask 4. The gas may be supplied from a central supply wall connector 5 or from a bottled source 6.

As the diameter of nasal cannula tubing is generally much smaller than respiratory circuits, (2-5 mm ID), it is difficult to transport aerosol along a length of nasal cannula tubing without considerable losses to condensate formed as liquid droplets. These liquid droplets can lead to patient discomfort.

This invention provides aerosolization into a chamber 10, which sits in the circuit from the supplemental oxygen supply or humidifier, if used, but is separate from the humidifier. The supplemental oxygen passes through the chamber 10, in which the aerosol generator 9 is located, and collects the aerosol transporting it to the patient. The chamber 10 is designed to selectively allow only smaller aerosol particle sizes (less than 3 microns), suitable for transport along narrow bore tubing, onto to the patient whilst encouraging localised deposition of the aerosol heavier particles.

Various medicaments available in liquid form may be aerosolised for use in therapies. Where the liquid being aerosolised is water, saline or other solution of water or saline, the aerosol generator also provides additional humidity to the circuit which may enhance patient comfort where no other humidity source is present.

Selection of smaller particle sizes may be achieved through use of the following or any combination of the following.

Figure 2:
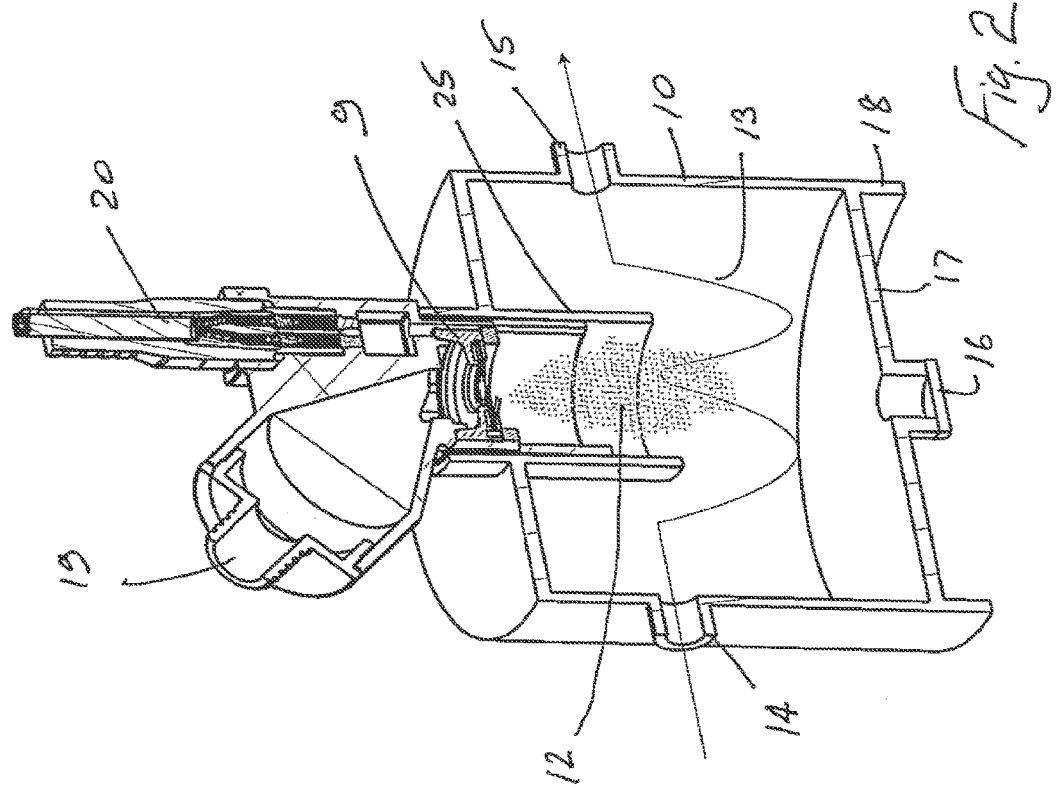
FIG. 2 is an isometric, partially cut-away view of part of a nasal cannula system according to one embodiment of the invention.

Referring to FIG. 2 in one embodiment of the invention aerosol from an aerosol generator 9 is delivered into a chamber 10, which sits in the circuit from the supplemental oxygen supply. The supplemental oxygen passes through this chamber 10, collects the aerosol and transports it to the patient 1 along the small bone tubing 2.

The aerosol generator 9 is mounted to the housing 10 and delivers aerosol 12 into an oxygen stream 13 flowing between an inlet 14 and an outlet 15 of the housing 10. The housing 10 also has a removable plug 16 in the base 17 thereof for draining any liquid that accumulates in the housing 10. The housing 10 also has support feet 18 so that the housing can be stood on a suitable surface. The aerosol generator 9 in this case has an optional adapter 19 for continuous feed, for example from a drip bag. The generator also has a power cable 20 which may connect to an AC/DC adapter or to a control module.

In one case the inlet 14 and outlet 15 are horizontally opposed. A separation plane, provided by a depending skirt 25 positioned between the inlet 14 and outlet 15 acts as a baffle to retard particles above a certain size whilst allowing the smaller particles to pass through for transport along the circuit. The majority of particles that exit the housing 10 are less than 3 microns. This is achieved through the combination of impaction on the separation wall 25 and the sharp change in flow direction created by the presence of the wall 25.

Figure 3:
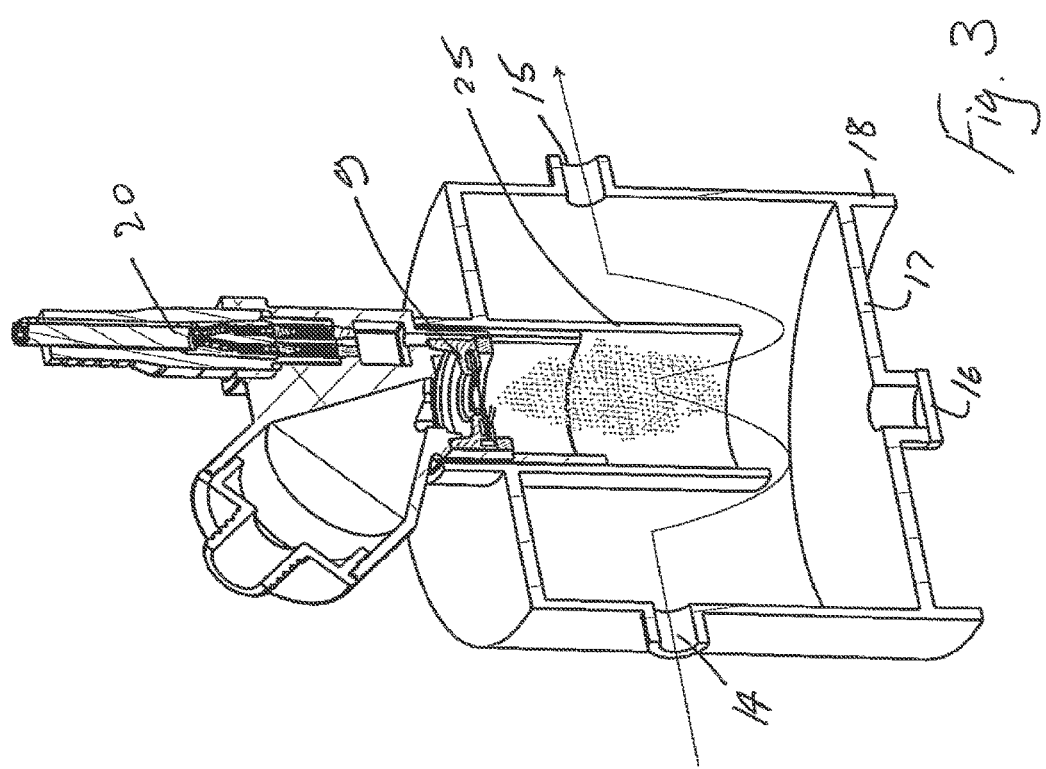
FIGS. 3 to 6 are isometric, partially cut-away views similar to FIG. 2 of part of nasal cannula systems according to other embodiments of the invention.

Referring to FIG. 3, the separation wall 25 may be extended further towards the floor of the chamber to produce a greater impaction surface and flow disturbance.

Figure 4:
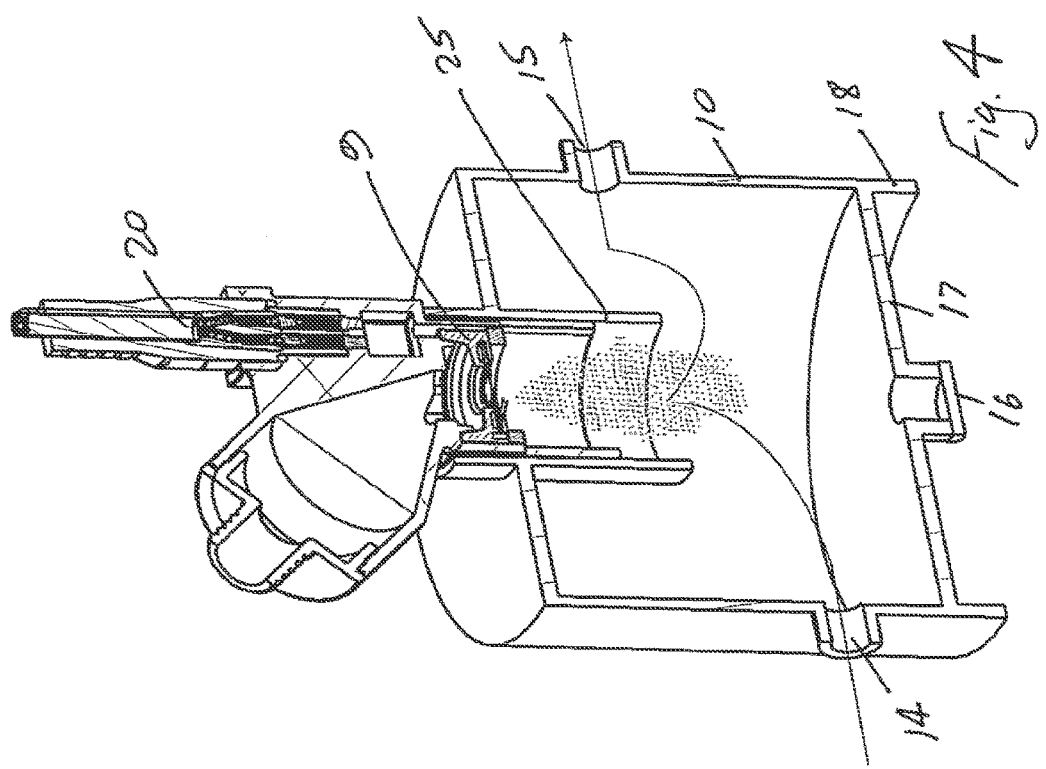

Referring to FIG. 4 the inlet 14 may be positioned at a substantially lower level (z-direction) relative to the separation plane and the outlet 15 to further adjust the impaction surface and flow disturbance.

Figure 5:
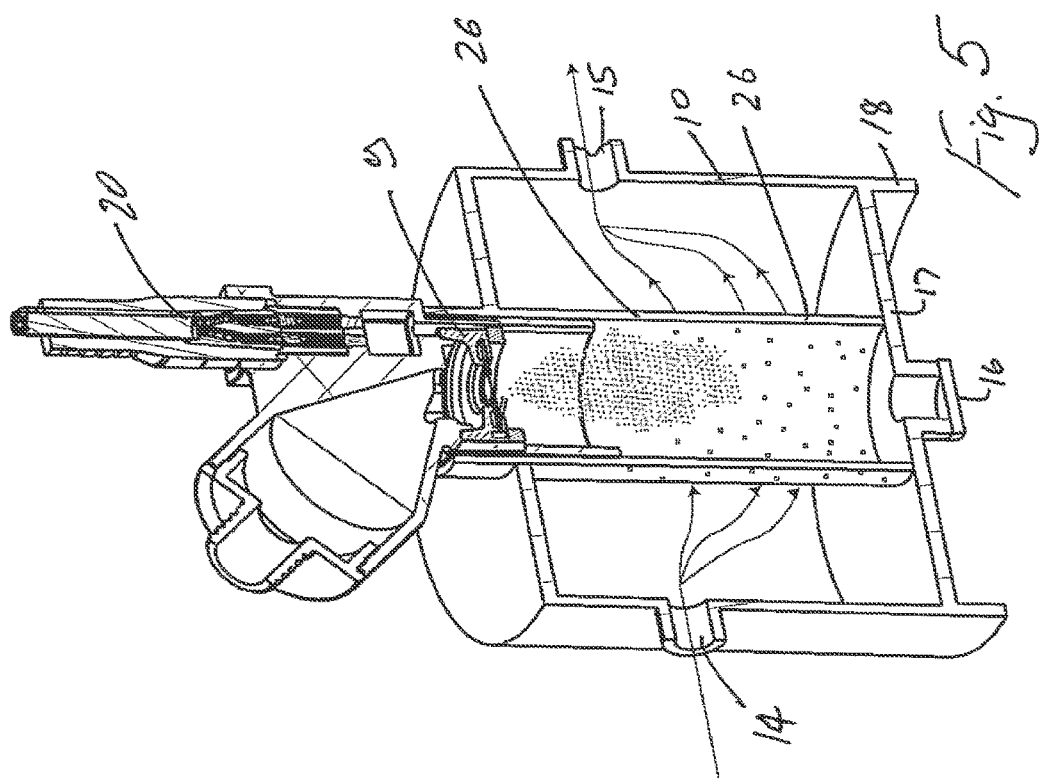

Referring to FIG. 5 in one case a separation wall 26 extends to and is joined to the floor of the chamber 10 to isolate the aerosol generation space from the airflow space. The separation wall in this case is porous, mesh or slotted to retard larger particles and allow smaller particles through to the outlet 15.

Figure 6:
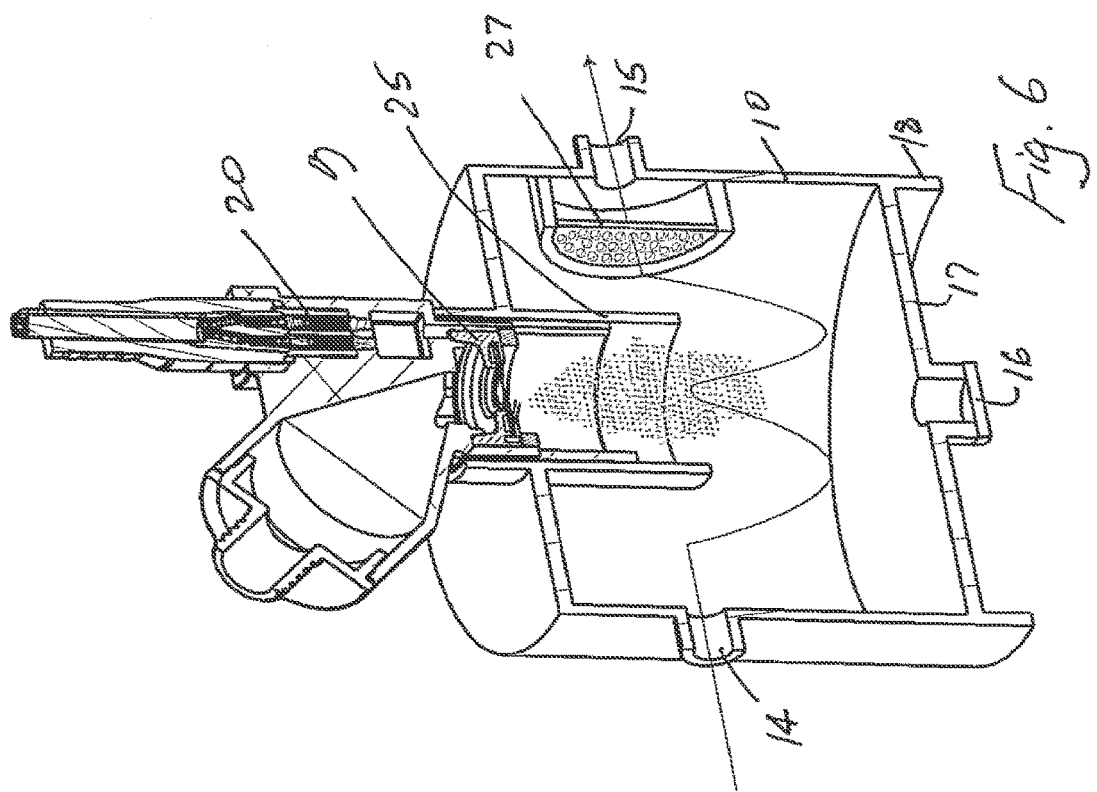
Figure 7:
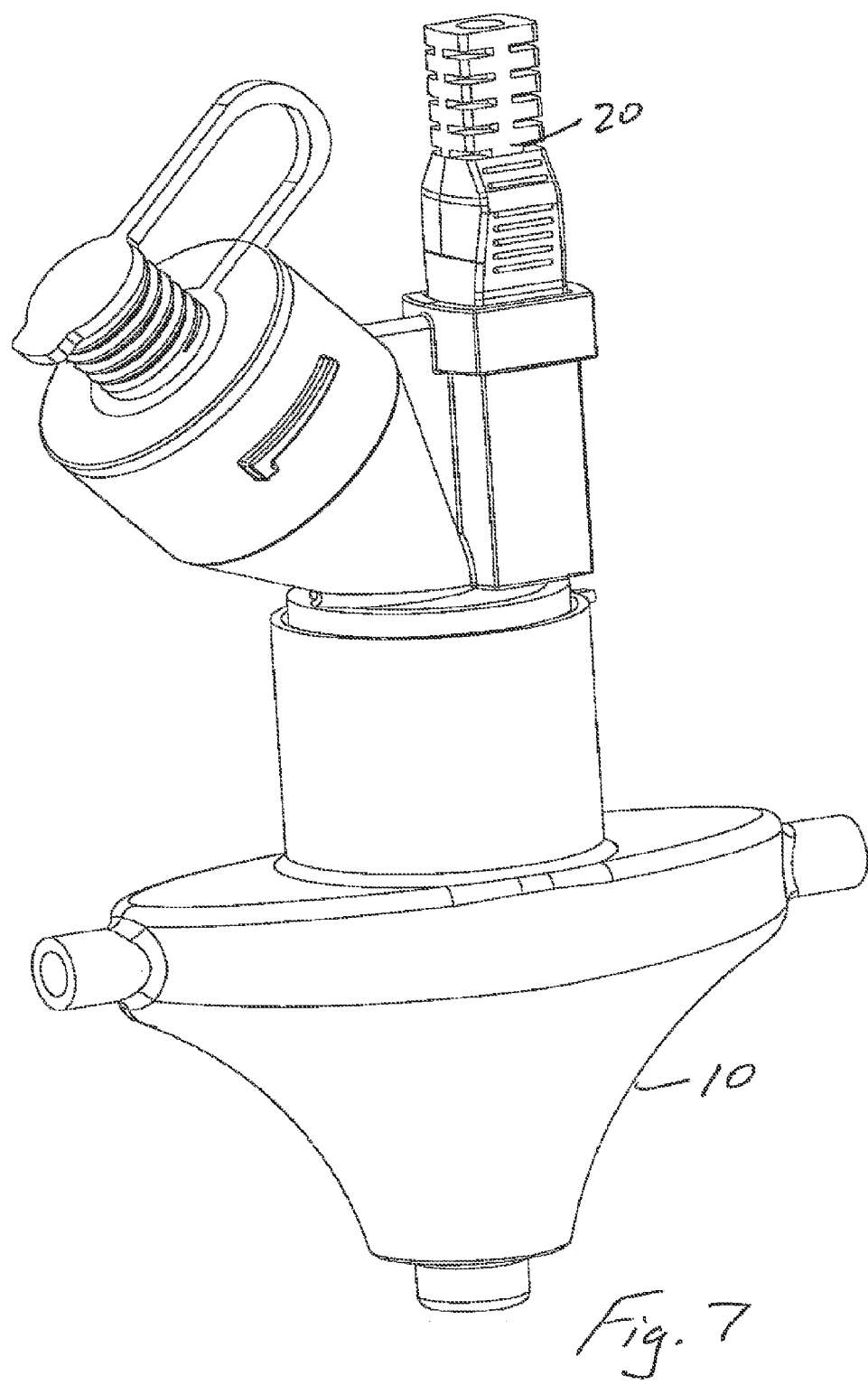
FIG. 7 is an isometric view of part of another nasal cannula system according to the invention.
Figure 8:
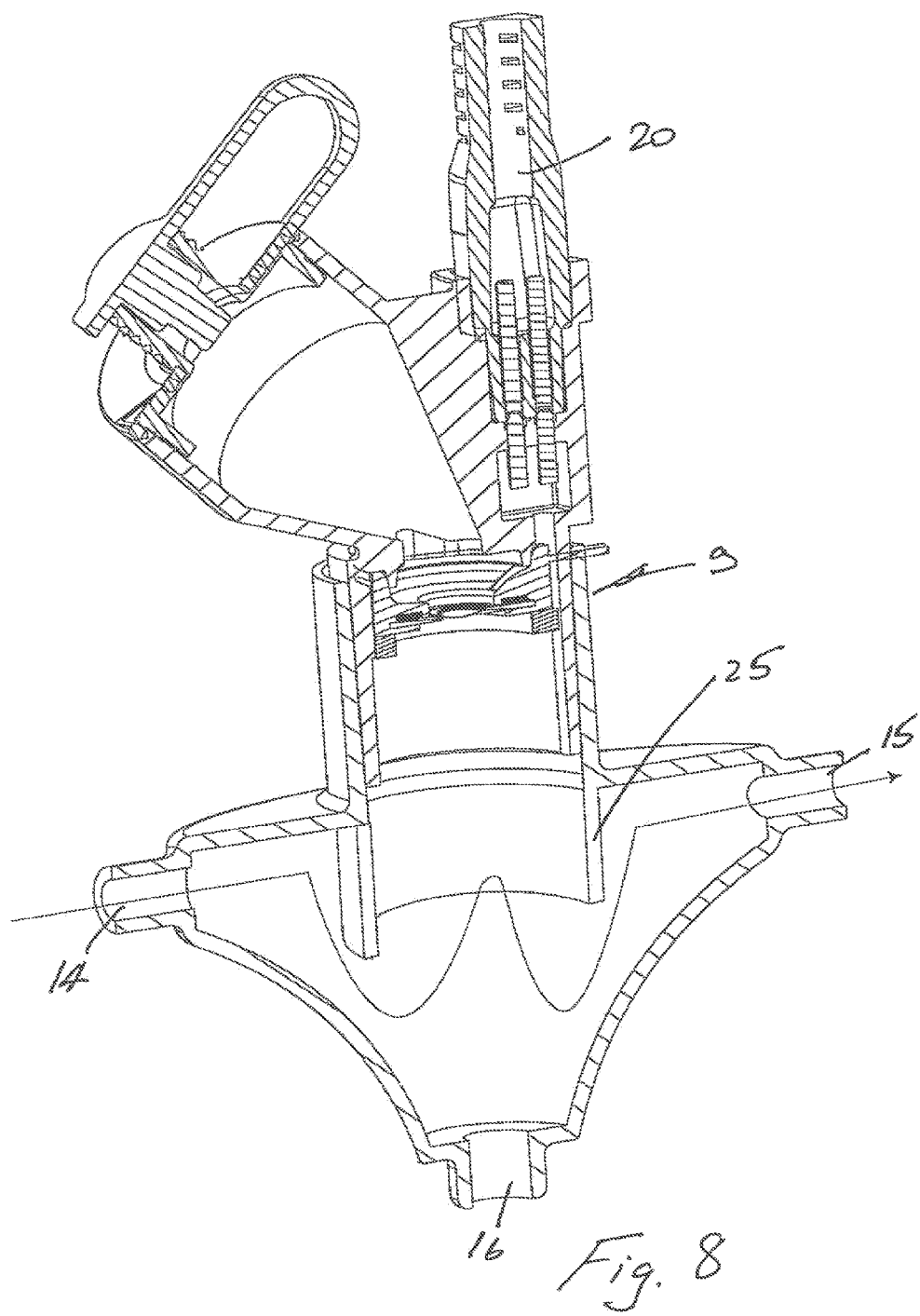
FIGS. 8 to 11 are cross sectional views of FIG. 7 illustrating system parts according to the various embodiments of the invention.
Figure 9:
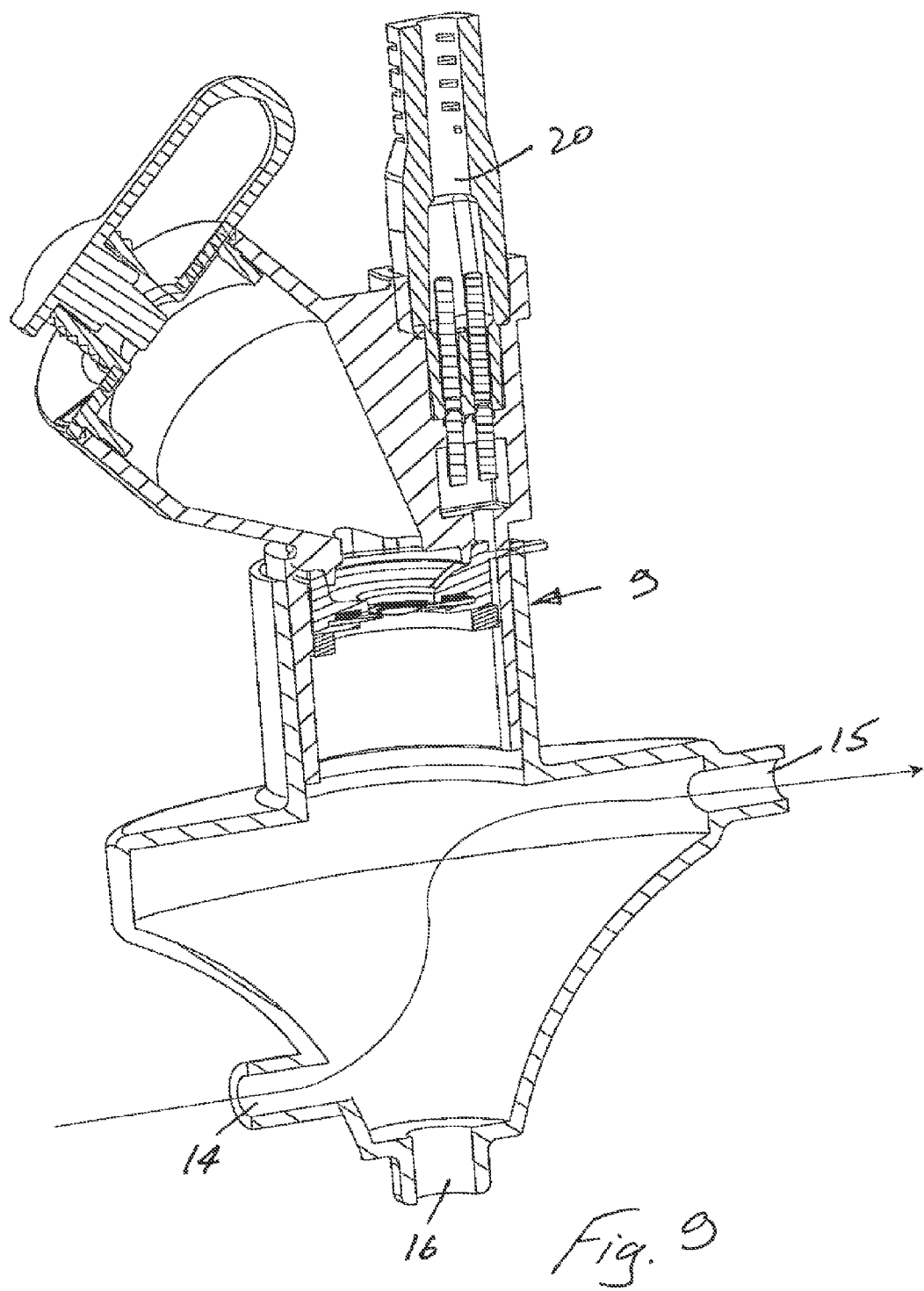
Figure 10:
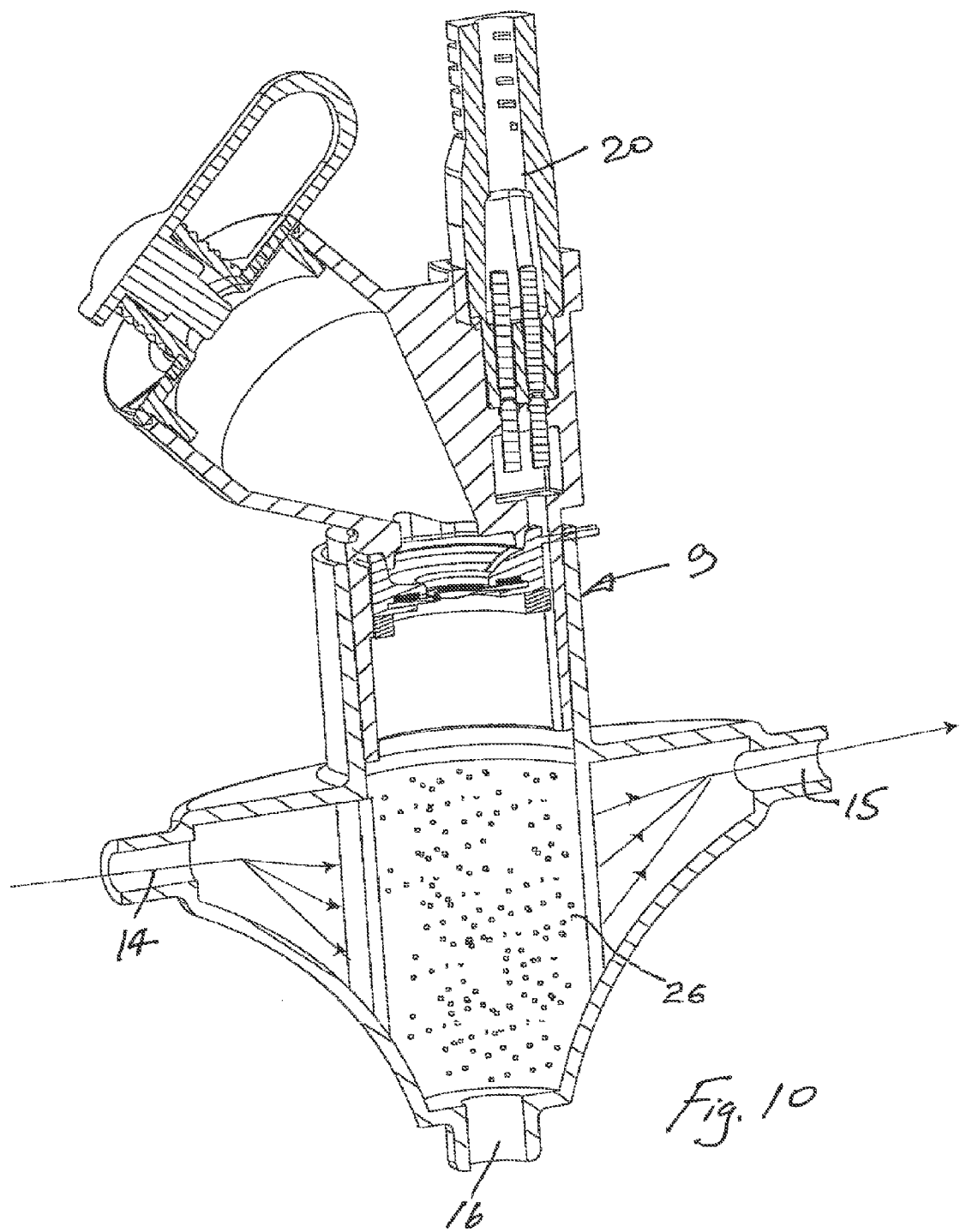
Figure 11:
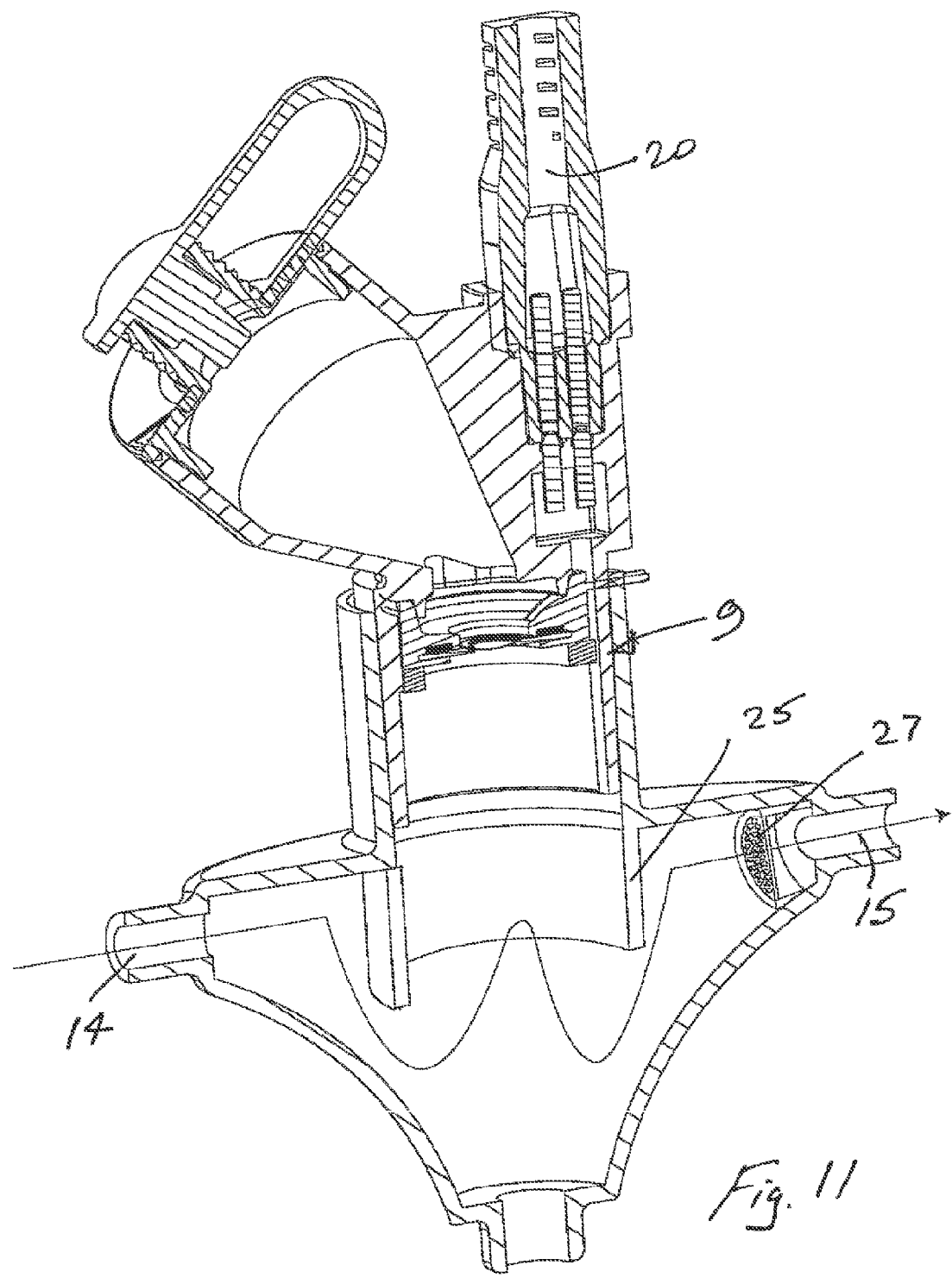
Figure 12:
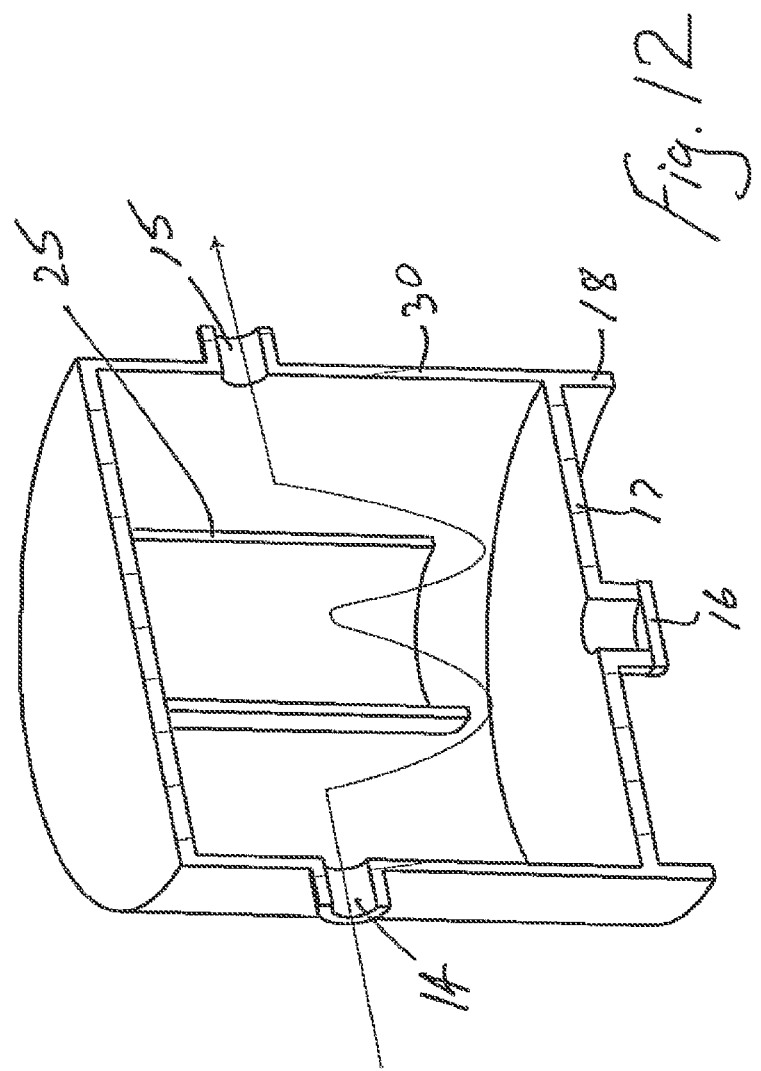
FIG. 12 is an isometric, partially cut-away view of part of another nasal cannula system according to the invention.
Figure 13:
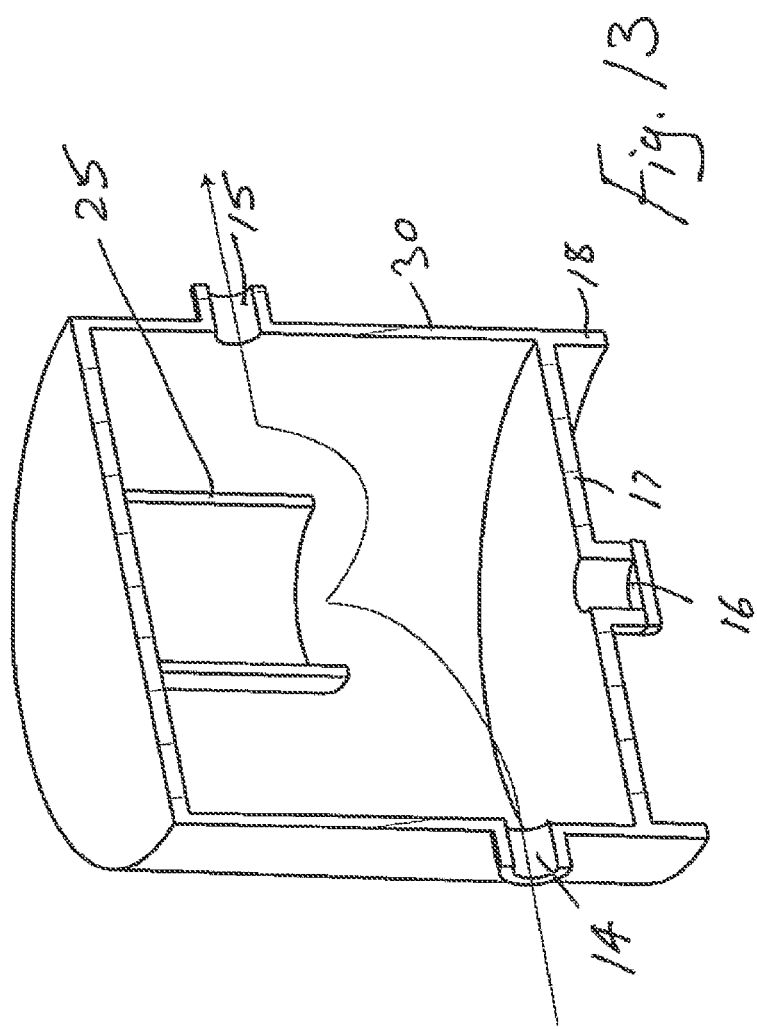
FIGS. 13 to 16 are isometric, partially cut-away views similar to FIG. 12 of part of nasal cannula systems according to other embodiments of the invention.
Figure 14:
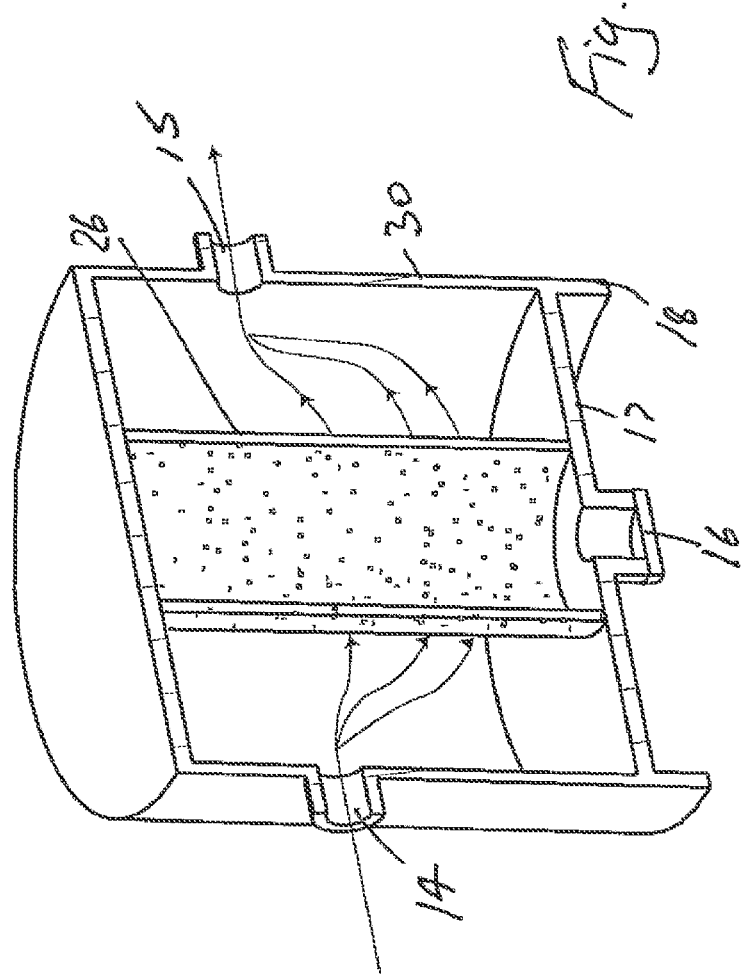
Figure 15:
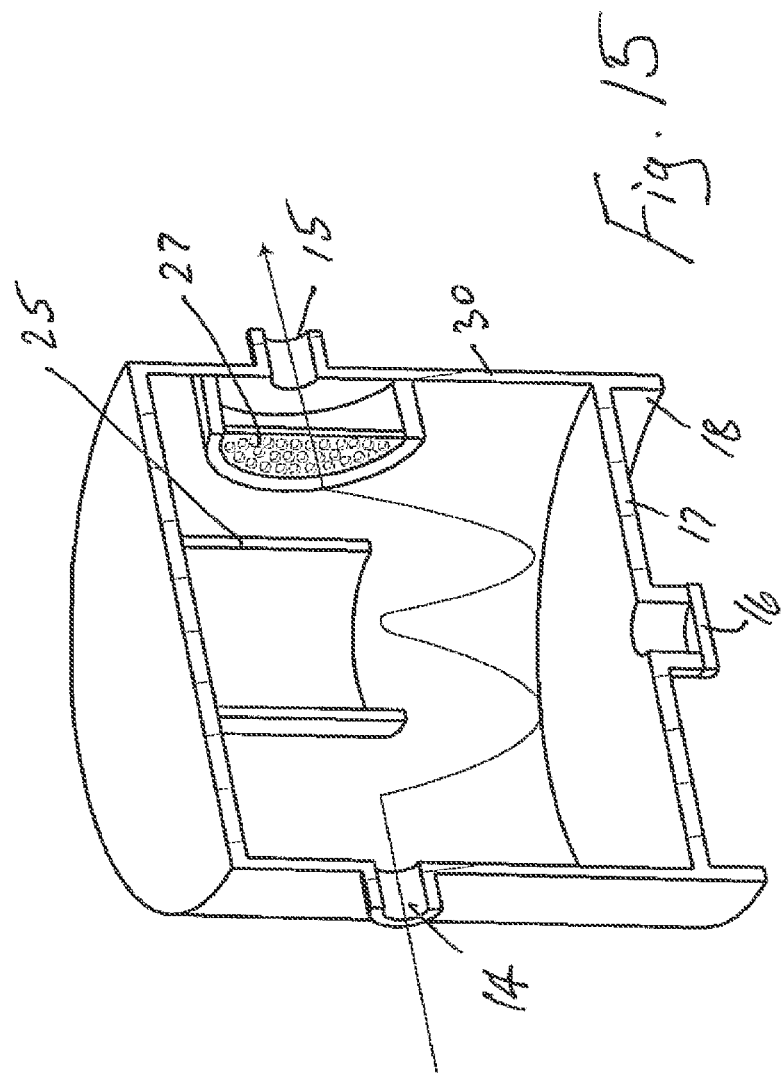
Figure 16:
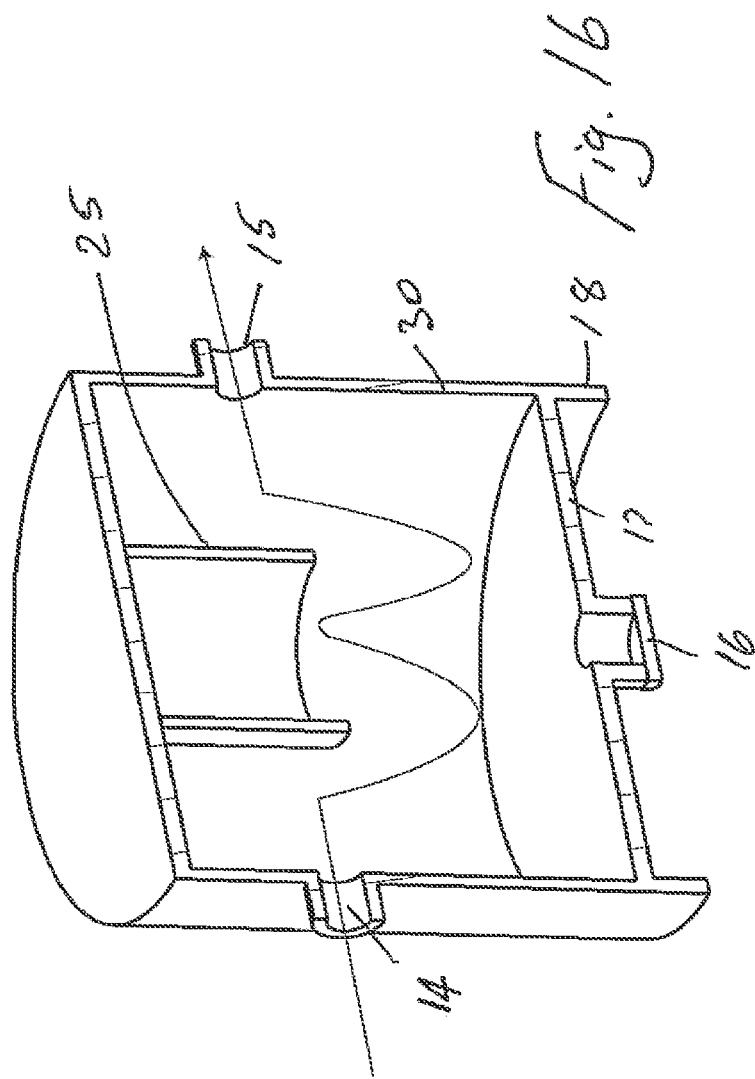

Referring to FIG. 6 there may be a screen, mesh or slotted plate 27 positioned over the outlet 15 to retard larger particles and allow smaller particles through to the circuit.

FIGS. 2 to 6 illustrate some features of an aerosol chamber but the design is not limited to this profile. Some or all of the elements may be incorporated into a lower profile design such as the example illustrated in FIGS. 7 to 11 in which elements similar to those described above with reference to FIGS. 2 to 6 are assigned the same reference numerals.

In a separate embodiment, the aerosol can be generated in isolation (for example in a t-piece fitting), which sits in the circuit from the supplemental oxygen supply or humidifier, if used, where there is no aerosol particle selection mechanism. Various chambers 30 of this type are illustrated in FIGS. 12 to 16. The particle separation chamber 30 is located in the circuit between the aerosol generator and the patient as a stand-alone element and receives a mixture of the therapy gas and the full spectrum of generated aerosol particle sizes. The chamber 30 selectively allows only smaller aerosol particle sizes, suitable for transport along narrow bore tubing, onto the patient whilst encouraging localised deposition of the aerosol heavier particles. The stand-alone chamber 30 may incorporate any combination of the elements described with reference to FIGS. 2 to 11.

Figure 17:
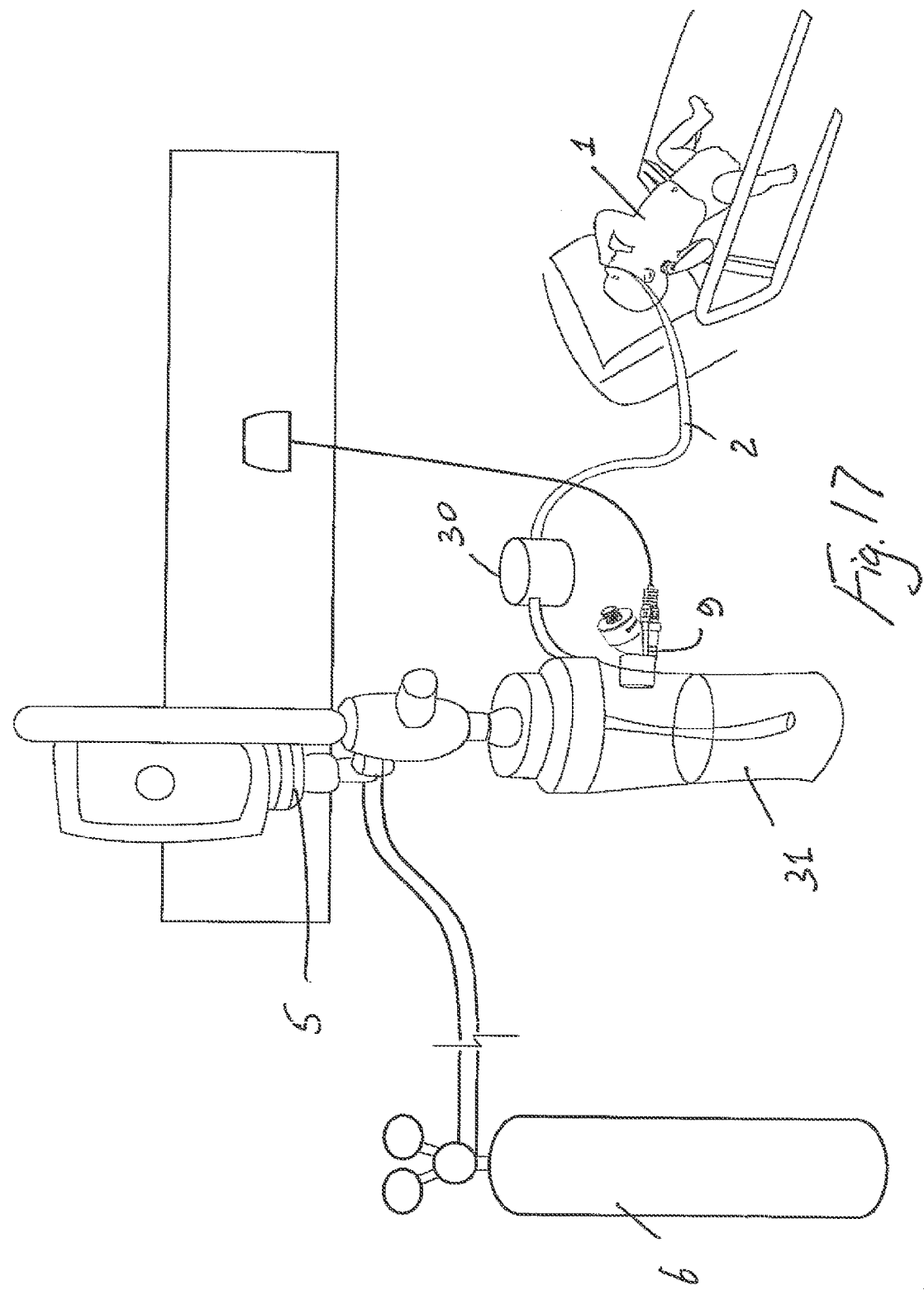
FIG. 17 is a diagram of a nasal cannula system according to a further embodiment of the invention.

Patients using a nasal cannula for delivery of oxygen in some cases have the oxygen passed through a bubble humidifier to humidify the oxygen, preventing drying out of the nasal mucus membranes. Referring to FIG. 17 in one embodiment of the invention aerosolisation from an aerosol generator 9 may be delivered directly into a bubble humidifier 31 which is supplied with oxygen from an oxygen supply 5 or 6. The aerosol is entrained with the humidified oxygen as it exits the bubble humidifier 31, passing into a cannula 2 to the nasal prongs for delivery to a patient 1.

The invention allows for aerosolization directly into a chamber suitable for use as a bubble humidifier. This may involve adaptation of existing and commonly available bubble humidifiers to allow addition of the aerosol generator (FIG. 17). This device may be used in combination with an additional downstream baffle box 30 as described with reference to any of FIGS. 12 to 16.

Figure 18:
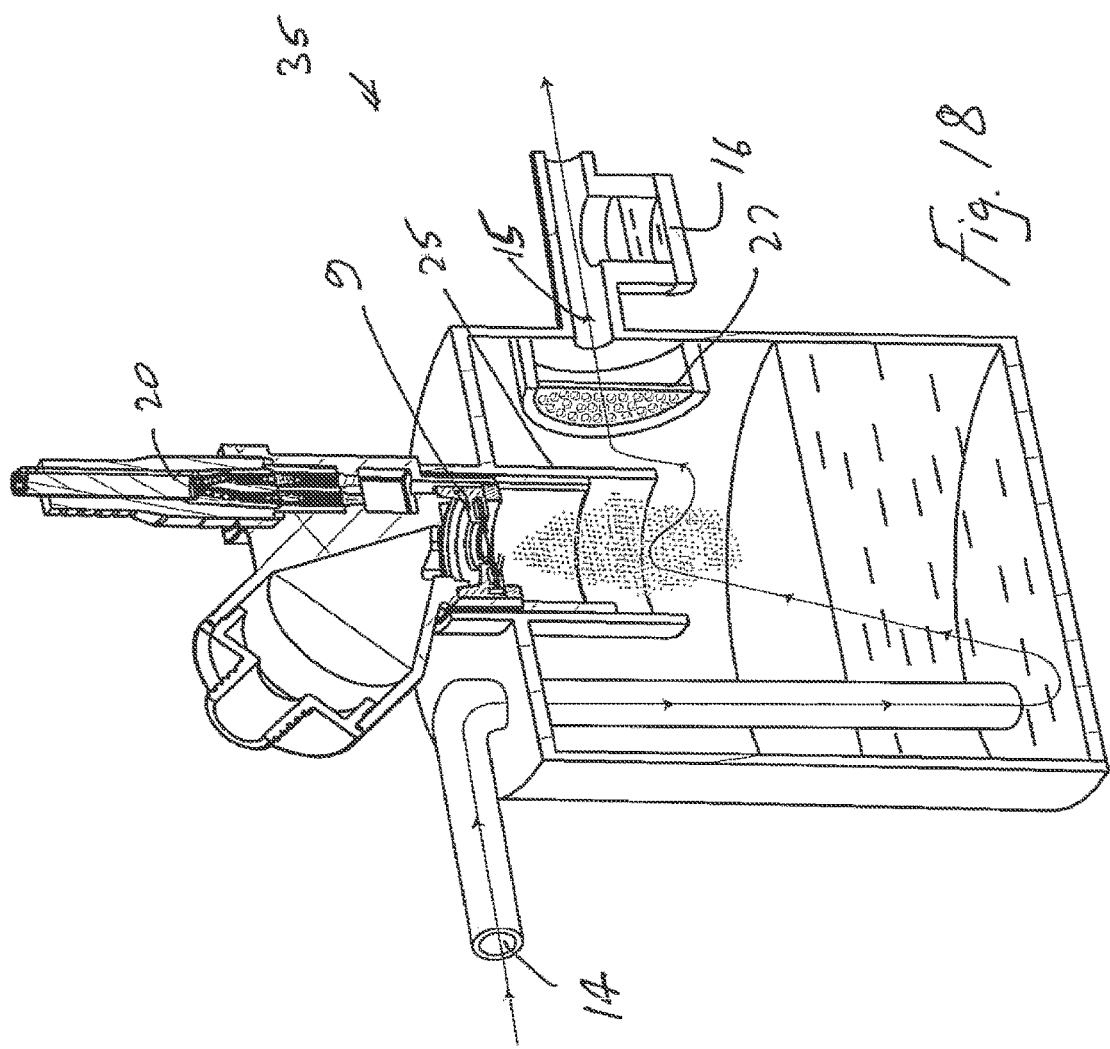
FIG. 18 is an isometric, partially cross sectional view of a nasal cannula system according to another embodiment of the invention.

Referring to FIG. 18 a bubble humidifier 35 may incorporate any combination of the elements outlined above.

Vibrating mesh technology which is described in detail below generates an aerosol with a precisely controlled particle size range optimised in general respiratory use for deep lung deposition. The distribution of particles can be represented as a normal distribution with the majority of particles produced in the range 2-10 microns. Test data has shown that the baffle box is effective in removing the larger particles to both lower the effective mean volumetric diameter and also change the distribution of particles to only allow those sizes suitable for transport along narrow bore tubing, onto to the patient with minimal rain-out along the tubing.

EXAMPLE

Profile/distribution of Generated Aerosol Before and After Action of Baffle Box

Figure 19:
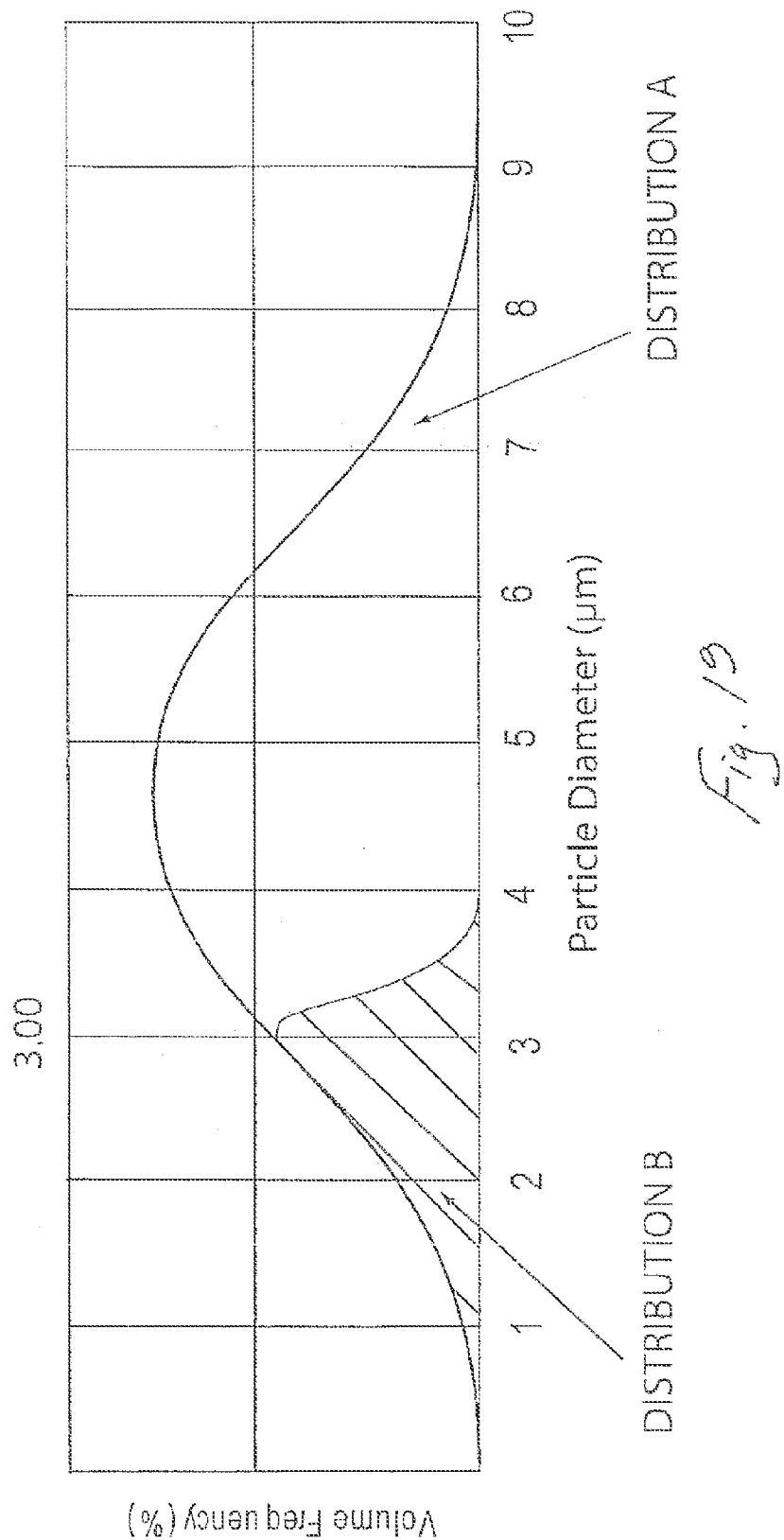
FIG. 19 is a graph of volume frequency for particle diameters for a known aerosol system (distribution A) and one aerosol system (distribution B) according to the invention.

Referring to FIG. 19 distribution A represents the normal distribution of aerosol particle diameters as produced by an aerosol generator. This test was carried out using a commercially available Aerogen SOLO nebuliser product for general respiratory use. Particle sizes fall broadly in the range of 1-10 microns. The term "span" is used to describe the spread of the particle size and is defined as (Dv90-Dv10)/Dv50. Dv90 is the volume diameter below which 90% of all particle diameters fall, Dv10 is the volume diameter below which 10% of all particle diameters fall and Dv50 is volume diameter below which 50% of all particle diameters fall.

Typically the Dv50 value is reported as the Volumetric Mean Diameter (VMD). For a specific aerosol generator under test at Aerogen the span was recorded as 2.27 and the VMD as 4.85 microns.

Distribution B represents the distribution of aerosol particle diameters produced by the test aerosol generator as measured after exiting the baffle box chamber. This testing was carried out using a commercially available Aerogen SOLO nebuliser product fitted to a chamber configured with lower inlet position, flow diversion and a screen as represented in FIGS. 4 & 6. Larger particles are removed from the distribution and only particles suitable for transport along narrow bore tubing are passed through the baffle box. For the specific aerosol generator under test the span was reduced to 0.76 and the VMD was reduced to 3 microns.

In the invention aerosol is delivered through single narrow bore tubing at flow rates up to 3 l pm, such that rainout is minimized and drug deposition is maximised at the delivery point of a face mask or a nasal cannula.

The invention has the following advantages:—
- Drug delivery via nasal cannula is not currently performed
- For convenience, patients may have medication delivered via the nasal cannula or narrow bore tubing to a face mask without the use of a separate nebulizer combined with a mouthpiece or mask.
- No disruption to the oxygen delivery to patients using nasal cannulas who have to use a separate face-mask when receiving nebulized medication.
- Improve patient comfort by reducing occurrence of liquid droplets entering the nasal passage through selectively sorting particle sizes better suited to transportation along narrow-bore tubing.
- Vibrating mesh aerosol generator does not require any gas flow to create aerosol. Can be used with very low in circuit gas flows.
- Designed to work with standard off-the-shelf cannulas with single bore tubing without need for re-circulation systems.
- Prevent condensate from forming in tubing through selection of aerosol particle sizes rather than gathering condensate in a trap near to the patient.
- Simple system without cost and complexity of heated humidification, drug delivery and re-circulation.
- Aerosol vibrating mesh technology maintains separation of medication reservoir from circuit to avoid contamination. There is no recirculation circuit required.
- Aerosol vibrating mesh technology has zero residual drug volume in the reservoir. This ensures precise control of delivered dose and good control of delivery for small doses. (expensive drugs).
- Vibrating mesh technology generates an aerosol with a precisely controlled particle size range optimised in general respiratory use for deep lung deposition.

The invention may be used in emergency wards for patients undergoing oxygen treatment via nasal cannula and respite care of same in mechanical ventilation.

In one aspect of the invention, an aerosol generator 9 is used to deliver an aerosolised humidifying agent into the gas. The humidifying agent may be sterile water or sterile saline with a salt concentration in the range from 1 micromolar to 154 millimolar. Such saline concentrations can be readily nebulised using the aerosolisation technology used in the invention.

Any suitable medicament, therapeutic agent, active substance or pharmaceutically active compound than can be nebulised may be employed. It can also act to deliver any agent presented in an aqueous drug solution.

The system facilitates delivery in aerosol form of, for example, bronchodilators, including β-agonists, muscarinic antagonists, epinephrine;, surfactants; pain-relief medications including anaesthetics; migraine therapies; anti-infectives; anti-inflammatories, steroids, including corticostroids; chemotherapeutic agents; mucolytics; vasodilators; vaccines and hormones. In addition substances classified as anti-thrombogenic agents, anti-proliferative agents, monoclonal antibodies, anti-neoplastic agents, anti-mitotic agents, anti-sense agents, anti-microbial agents, nitric oxide donors, anti-coagulants, growth factors, translational promoter, inhibitors of heat shock proteins, biomoloecules including proteins, polypeptides and proteins, oligonucleotides, oligoproteins, siRNA, anti-sense DNA and RNA, ribozymes, genes, viral vectors, plasmids, liposomes, angiogenic factors, hormones, nucleotides, amino acids, sugars, lipids, serine proteases, anti-adhesion agents including but not limited to hyaluronic acid, biodegradable barrier agents may also be suitable.

The medicament may for example, comprise long-acting beta-adrenoceptor agonists such as salmeterol and formoterol or short-acting beta-adrenoceptor agonists such as albuterol.

The medicament may be a long-acting muscarinic antagonists such as tiotropium (Spiriva) or short-acting muscarinic antagonists such as ipratropium (Atrovent).

Typical anti-infectives include antibiotics such as an aminoglycoside, a tetracycline, a fluroquinolone; anti-microbials such as a cephalosporin; and anti-fungals. Examples of antibiotics include anti-gram-positive agents such as macrolides, e.g. erythromycin, clarithromycin, azithromycin, and glycopeptides, e.g. vancomycin and teicoplanin, as well as any other anti-gram-positive agent capable of being dissolved or suspended and employed as a suitable aerosol, e.g. oxazoldinone, quinupristin/dalfopristen, etc. Antibiotics useful as anti-gram-negative agents may include aminoglycosides, e.g. gentamicin, tobramycin, amikacin, streptomycin, netilmicin, quinolones, e.g. ciprofloxacin, ofloxacin, levofloxacin, tetracyclines, e.g. oxytetracycline, dioxycycline, minocycline, and cotrimoxazole, as well as any other anti-gram-negative agents capable of being dissolved or suspended and employed as a suitable aerosol.

Anti-inflammatories may be of the steroidal such as budesonide or ciclesonide, non-steroidal, such as sodium cromoglycate or biological type.

Typical local anaesthetics are, for example, Ropivacaine, Bupivacaine, levobupivacaine, and Lidocaine.

Chemotherapeutic agents may be alkylating agents, anti-metabolites, anthracyclines, plant alkaloids, topoisomerase inhibitors, nitrosoureas, mitotic inhibitors, monoclonal antibodies, tyrosine kinase inhibitors, hormone therapies including corticosteroids, cancer vaccines, anti-estrogens, aromatase inhibitors, anti-androgens, anti-angiogenic agents and other anti-tumour agents.

Surfactant medications (sometimes referred to herein as "surfactants") are protein-lipid compositions, e.g. phospholipids, that are produced naturally in the body and are essential to the lungs' ability to absorb oxygen. They facilitate respiration by continually modifying surface tension of the fluid normally present within the air sacs, or alveoli, that tube the inside of the lungs. In the absence of sufficient surfactant, these air sacs tend to collapse, and, as a result, the lungs do not absorb sufficient oxygen. Insufficient surfactant in the lungs results in a variety of respiratory illnesses in both animals and humans. Since most of these surfactant medications are animal-based, the current supply is limited, and although synthetic surfactants are available, their manufacture is both inexact and expensive. In addition, the surfactant medications are typically high in viscosity and are difficult to deliver to the patient's respiratory system. The increased efficiency of the pressure-assisted breathing system of the present invention, and the smaller amount of medicament required for a treatment according to the present invention, can be a substantial advantage when such scarce and expensive medicaments are employed. The combination of surfactant with other medicaments to improve distribution in the lung and body is also possible. Surfactants also possess the capacity to act as anti-adhesion agents.

In the invention an aerosol is delivered into the nasal cannula circuit. The distinction between aerosol and vapour is in the size of the particles. The majority of aerosol particles that the aerosol generator produces are in the 0.5 to 5.0 micron diameter range. Water vapour on the other hand contains individual water molecules which are approximately 0.00001 microns i.e. 10,000 times smaller than the aerosol particles.

Referring to FIGS. 20 to 29, the apparatus comprises a reservoir 100 for storing sterile water or saline solution which may or may not contain a drug, the aerosol generator 9 for aerosolising the solution, and a controller 103 for controlling the operation of the aerosol generator 9.

This aerosol generator 9 converts the water into an aerosol of a very definable particle size. The volumetric median diameter (VMD) would typically be in the range of 2-10 microns.

The controller 103 is used to provide electrical power to drive the aerosol generator 9. This provides the aerosolising action to convey aerosol to the supplemental oxygen being delivered to a patient.

The nebuliser (or aerosol generator) 9, has a vibratable member which is vibrated at ultrasonic frequencies to produce liquid droplets. Some specific, non-limiting examples of technologies for producing fine liquid droplets is by supplying liquid to an aperture plate having a plurality of tapered apertures extending between a first surface and a second surface thereof and vibrating the aperture plate to eject liquid droplets through the apertures. Such technologies are described generally in U.S. Pat. Nos. 5,164,740; 5,938,117; 5,586,550; 5,758,637; -6755189, 6540154, 6926208, 7174888, 6546927, 6,085,740, and US2005/021766A, the complete disclosures of which are incorporated herein by reference. However, it should be appreciated that the present invention is not limited for use only with such devices.

In use, the liquid to be aerosolised is received at the first surface, and the aerosol generator 9 generates the aerosolised liquid at the second surface by ejecting droplets of the liquid upon vibration of the vibratable member. The apertures in the vibratable member are sized to aerosolise the liquid by ejecting droplets of the liquid such that the majority of the droplets by mass have a size of less than 5 micrometers.

Figure 22:
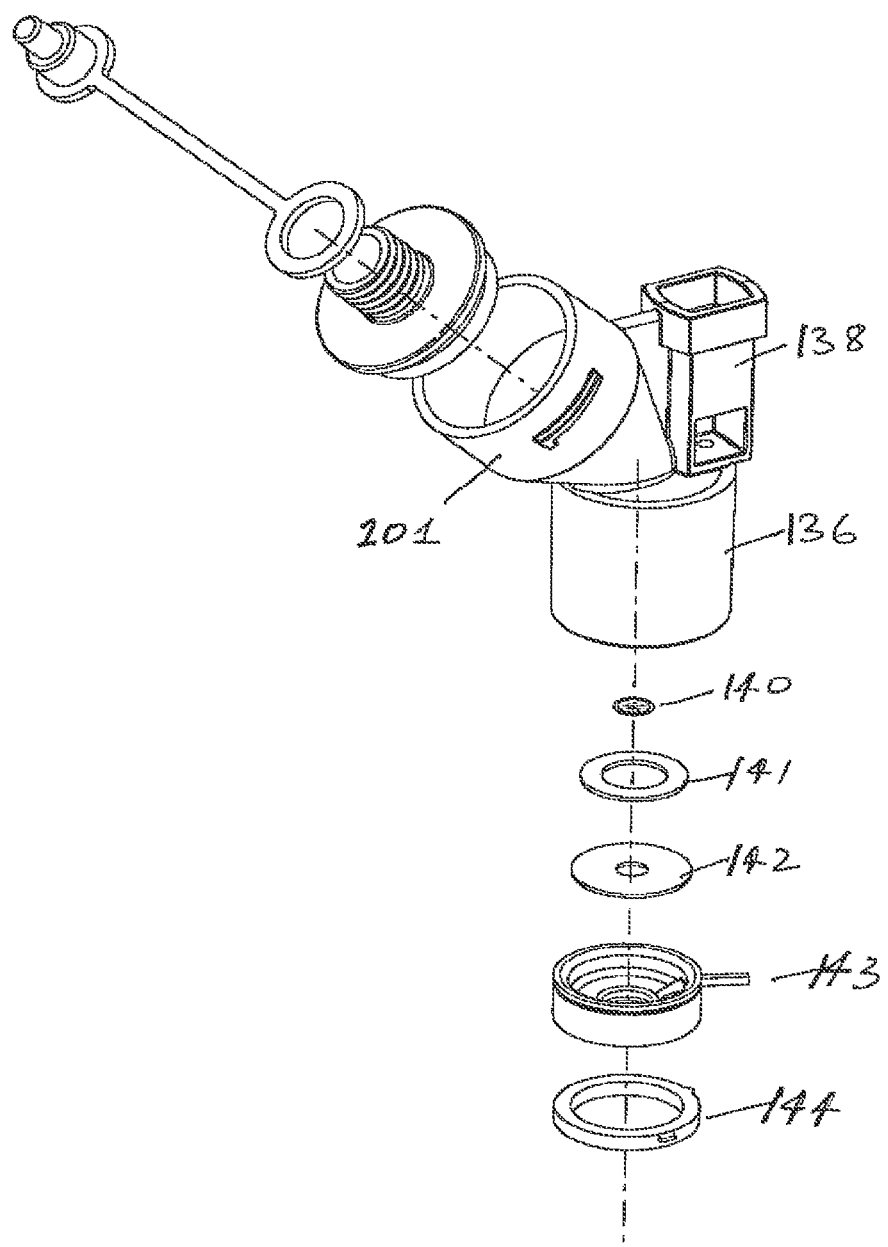
FIG. 22 is an exploded isometric view of an aerosol generator used in the invention.
Figure 23:
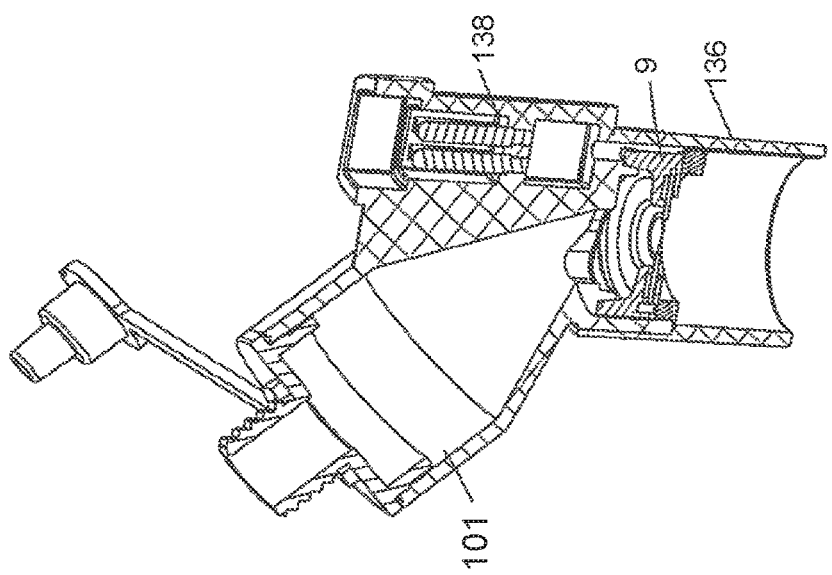
FIG. 23 is a cross-sectional view of the assembled aerosol generator of FIG. 22.

Referring particularly to FIGS. 22 and 23, in one case the aerosol generator 9 comprises a vibratable member 140, a piezoelectric element 141 and a washer 142, which are sealed within a silicone overmould 143 and secured in place within a housing 136 using a retaining ring 144. The vibratable member 140 has a plurality of tapered apertures extending between a first surface and a second surface thereof.

The first surface of the vibratable member 140, which in use faces upwardly, receives the liquid from the reservoir 101 and the aerosolised liquid, is generated at the second surface of the vibratable member 140 by ejecting droplets of liquid upon vibration of the member 140. In use the second surface faces downwardly. In one case, the apertures in the vibratable member 140 may be sized to produce an aerosol in which the majority of the droplets by weight have a size of less than 5 micrometers.

The vibratable member 140 could be non-planar, and may be dome-shaped in geometry.

The complete nebuliser may be supplied in sterile form, which is a significant advantage. The aerosol generator unit may comprise a collar or neck 136 to facilitate mounting of the unit, for example to the housings 20, 30. The interfitting may be a push fit. This enables the unit to be easily mounted and de-mounted, for example for cleaning. The neck or collar 136 at least partially lines the opening into the housing 20, 30 and may project inwardly to define an internal wall as described above.

Figure 20:
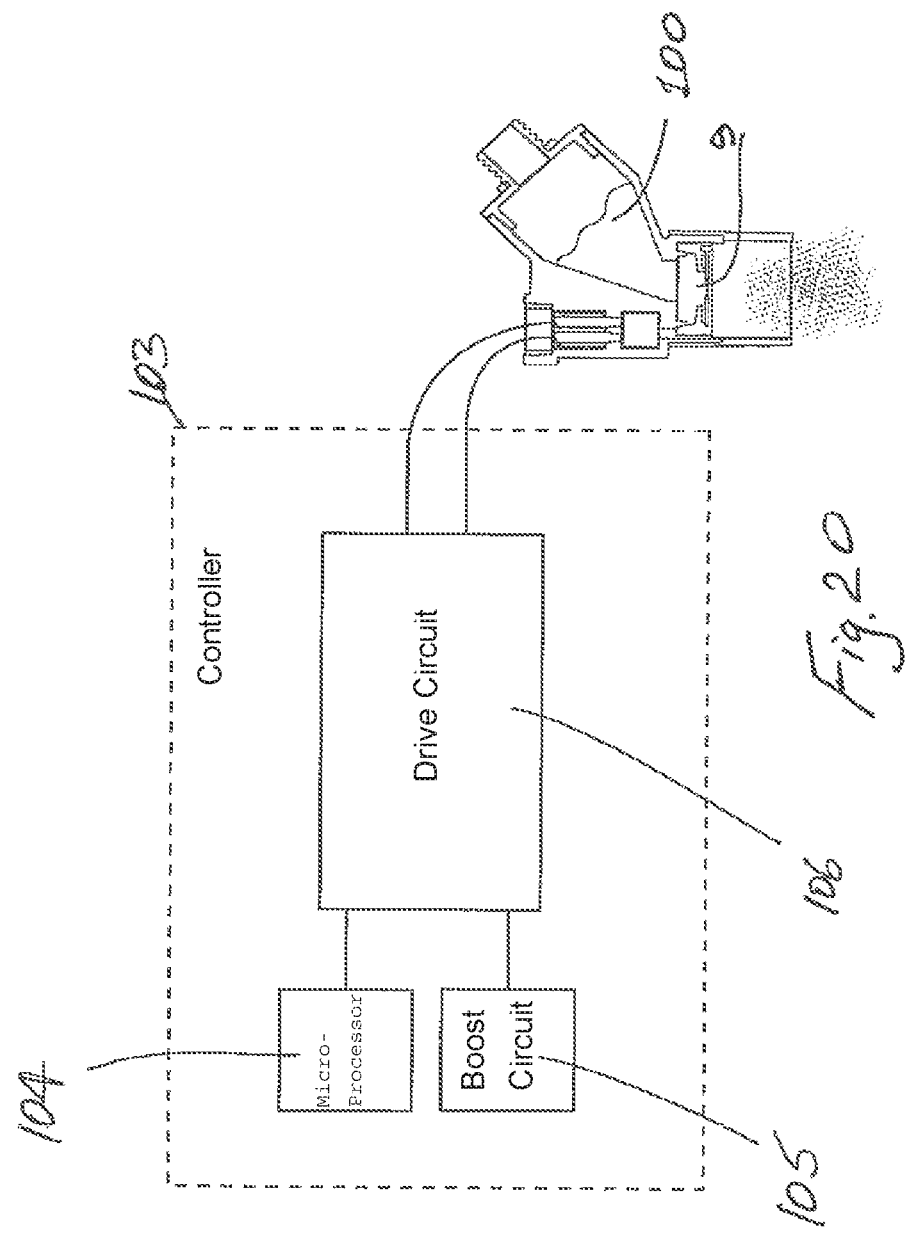
FIG. 20 is a schematic illustration of a part of an apparatus according to the invention.
Figure 21:
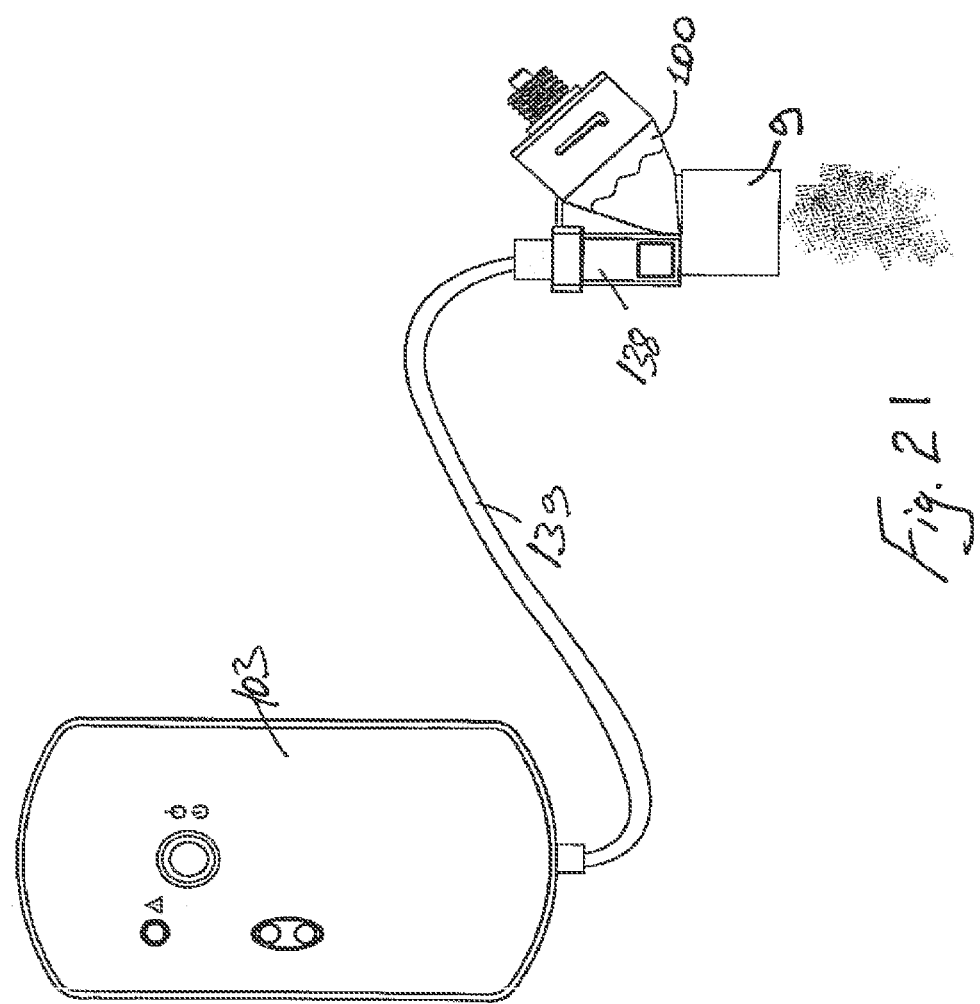
FIG. 21 is a schematic illustration of a part of the apparatus.

Referring particularly to FIG. 20, the controller 103 controls operation of and provides a power supply to the aerosol generator 9. The aerosol generator 9 has a housing which defines the reservoir 101. The housing has a signal interface port 138 fixed to the lower portion of the reservoir 101 to receive a control signal from the controller 103. The controller 103 may be connected to the signal interface port 138 by means of a control lead 139 which has a docking member 150 for mating with the port 138. A control signal and power may be passed from the controller 103 through the lead 139 and the port 138 to the aerosol generator 9 to control the operation of the aerosol generator 9 and to supply power to the aerosol generator 9 respectively.

The power source for the controller 103 may be an on-board power source, such as a rechargeable battery, or a remote power source, such as a mains power source, or an insufflator power source. When the remote power source is an AC mains power source, an AC-DC converter may be connected between the AC power source and the controller 103. A power connection lead may be provided to connect a power socket of the controller 103 with the remote power source.

Figure 24:
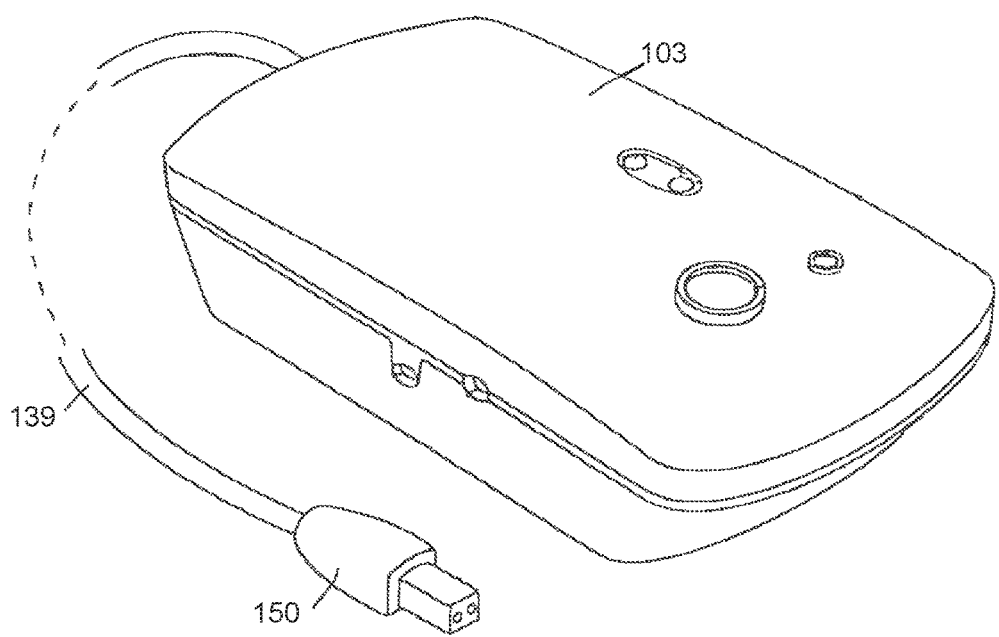
FIG. 24 is a perspective view of a controller housing used in the apparatus of the invention.

Referring particularly to FIG. 24 the controller 103 has a housing and a user interface to selectively control operation of the aerosol generator 9. Preferably the user interface is provided on the housing which, in use, is located remote from the aerosol generator housing. The user interface may be in the form of, for example, an on-off button. In one embodiment a button can be used to select pre-set values for simplicity of use. In another embodiment a dial mechanism can be used to select from a range of values from 0-100%. This embodiment has the advantage of providing the aerosol at a much lower flow rate which will 'rain out' less and alleviate the need for the baffle box system.

Status indication means are also provided on the housing to indicate the operational state of the aerosol generator 9. For example, the status indication means may be in the form of two visible LED's, with one LED being used to indicate power and the other LED being used to indicate aerosol delivery. Alternatively one LED may be used to indicate an operational state of the aerosol generator 9, and the other LED may be used to indicate a rest state of the aerosol generator 9.

A fault indicator may also be provided in the form of an LED on the housing. A battery charge indicator in the form of an LED may be provided at the side of the housing.

The liquid in the reservoir 101 flows by gravitational action towards the aerosol generator 9 at the lower medicament outlet. The controller 103 may then be activated to supply power and a control signal to the aerosol generator 9, which causes the piezoelectric element 141 to vibrate the non-planar member 140. This vibration of the non-planar member 140, causes the aqueous solution at the top surface of the member 140 to pass through the apertures to the lower surface where the aqueous solution is aerosolised by the ejection of small droplets of solution.

A flow rate sensor/meter may be used to determine the flow rate of the ventilation gas. In response to the fluid flow rate of the ventilation gas, the controller 103 commences operation of the aerosol generator 9 to aerosolise the aqueous solution. The aerosolised aqueous solution is entrained with the ventilation gas, and delivered to the patient.

In the event of alteration of the fluid flow rate of the ventilation gas, the flow rate sensor/meter determines the alteration, and the controller 103 alters the pulse rate of the vibratable member of the nebuliser accordingly.

The controller 103 is in communication with the flow rate sensor/meter. The controller 103 is configured to control operation of the aerosol generator 9, responsive to the fluid flow rate of the ventilation gas and also independent of the fluid flow rate of the ventilation gas as required.

In one case, the controller 103 is configured to control operation of the aerosol generator 9 by controlling the pulse rate at a set frequency of vibration of the vibratable member, and thus controlling the fluid flow rate of the aqueous solutions. This has the advantage of reducing 'rain out' such as by way of reduced aerosol velocity.

The controller 103 may comprise a microprocessor 104, a boost circuit 105, and a drive circuit 106. FIG. 20 illustrates the microprocessor 104, the boost circuit 105, the drive circuit 106 comprising impedance matching components (inductor), the nebuliser 9, and the aerosol. The inductor impedance is matched to the impedance of the piezoelectric element of the aerosol generator 9. The microprocessor 104 generates a square waveform of 128 KHz which is sent to the drive circuit 106. The boost circuit 105 generates a 12V DC voltage required by the drive circuit 106 from an input of either a 4.5V battery or a 9V AC/DC adapter. The circuit is matched to the impedance of the piezo ceramic element to ensure enhanced energy transfer. A drive frequency of 128 KHz is generated to drive the nebuliser at close to its resonant frequency so that enough amplitude is generated to break off droplets and produce the aerosol. If this frequency is chopped at a lower frequency such that aerosol is generated for a short time and then stopped for a short time this gives good control of the nebuliser's flow rate. This lower frequency is called the pulse rate.

The drive frequency may be started and stopped as required using the microprocessor 4. This allows for control of flow rate by driving the nebuliser 9 for any required pulse rate. The microprocessor 104 may control the on and off times to an accuracy of milliseconds.

The nebuliser 9 may be calibrated at a certain pulse rate by measuring how long it takes to deliver a know quantity of solution. There is a linear relationship between the pulse rate and the nebuliser flow rate. This may allow for accurate control over the delivery rate of the aqueous solution.

The nebuliser drive circuit consists of the electronic components designed to generate output sine waveform of approximately 100V AC which is fed to nebuliser 9 causing aerosol to be generated. The nebuliser drive circuit 106 uses inputs from microprocessor 104 and boost circuit 105 to achieve its output. The circuit is matched to the impedance of the piezo ceramic element to ensure good energy transfer.

The aerosol generator 9 may be configured to operate in a variety of different modes, such as continuous, and/or phasic, and/or optimised.

The pulse control is particularly relevant in the case where the aerosol generator itself provides a humidifier.

Figure 25A:
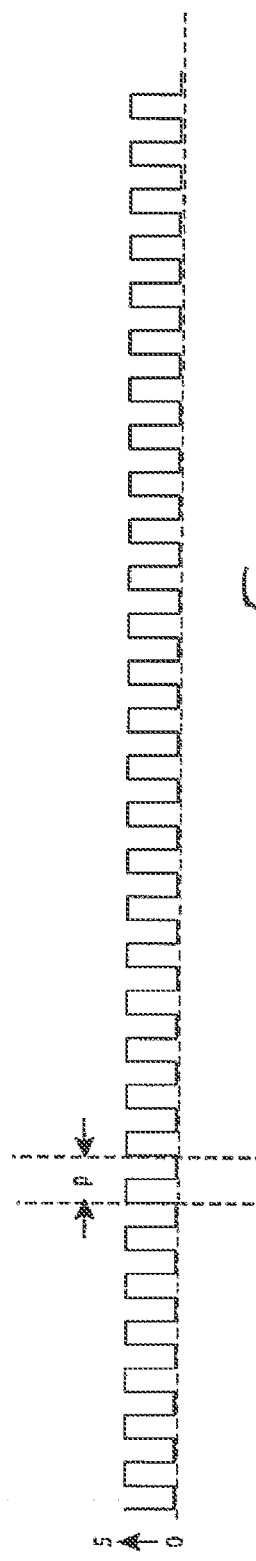
FIGS. 25(a) and 25(b) are graphs of DC voltage versus time and AC voltage versus time respectively to achieve a 100% aerosol output.
Figure 25B:
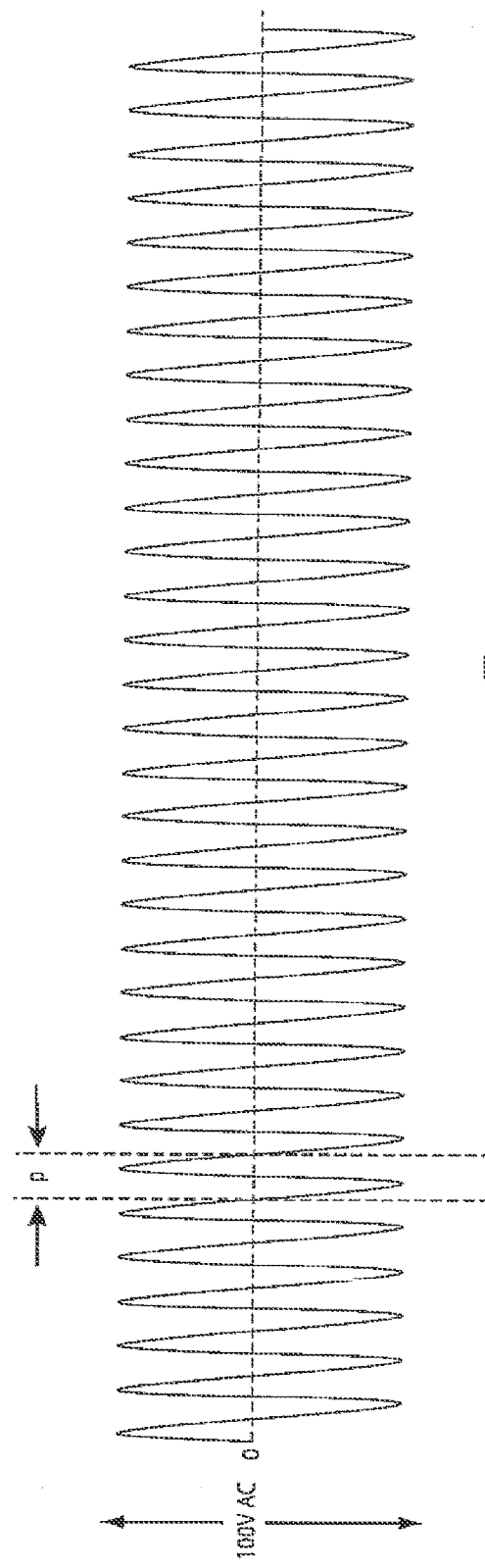

For example, referring to FIG. 25(a) illustrates a 5V DC square waveform output from the microprocessor 104 to the drive circuit 106. FIG. 25(b) shows a low power, ~100V AC sine waveform output from drive circuit 106 to nebuliser 9. Both waveforms have a period p of 7.8 µS giving them a frequency of 1/7.8 µs which is approximately 128 KHz. Both waveforms are continuous without any pulsing. The aerosol generator may be operated in this mode to achieve 100% aerosol output.

Referring to FIGS. 26(a) in another example, there is illustrated a 5V DC square waveform output from the microprocessor 104 to the drive circuit 106. FIG. 26(b) shows a low power, ~100V AC sine waveform output from the drive circuit 6 to the nebuliser 9. Both waveforms have a period p of 7.8 µS giving them a frequency of 1/7.8 µs which is approximately 128 KHz. In both cases the waveforms are chopped (stopped/OFF) for a period of time x. In this case the off time x is equal to the on time x. The aerosol generator may be operated in this mode to achieve 50% aerosol output.

Figure 27A:
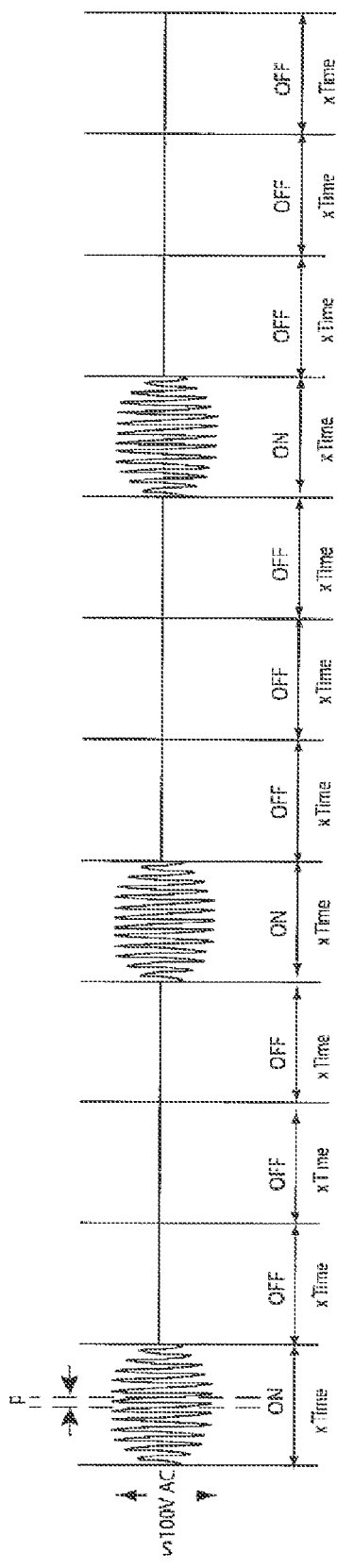
FIGS. 27(a) and 27(b) are graphs of DC voltage versus time and AC voltage versus time respectively to achieve a 25% aerosol output
Figure 27B:
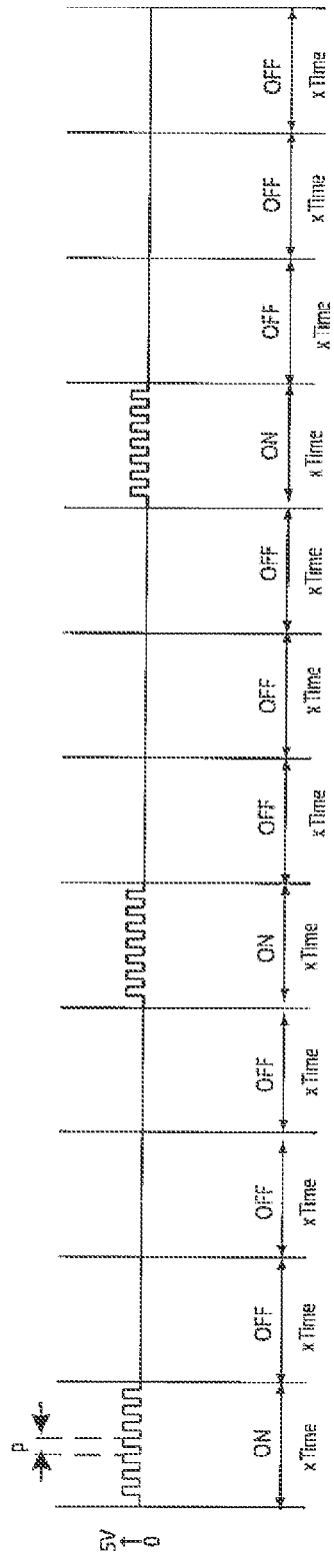

In another case, referring to FIGS. 27(a) there is illustrated a 5V DC square waveform output from microprocessor 104 to drive circuit 106. FIG. 27(b) shows a low power, ~100V AC sine waveform output from the drive circuit 106 to the nebuliser 9. Both waveforms have a period p of 7.8 µS giving them a frequency of 1/7.8 µs which is approximately 128 KHz. In both cases the wavefoms are chopped (stopped/OFF) for a period of time x. In this case the off time is 3x while the on time is x. The aerosol generator may be operated in this mode to achieve 25% aerosol output.

Figure 28:
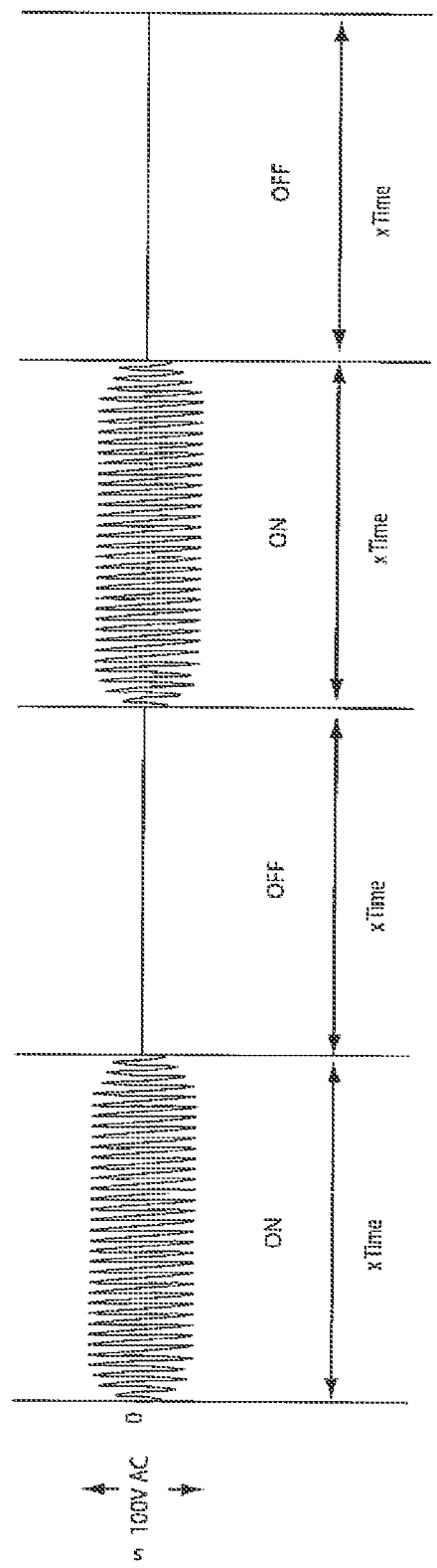
FIG. 28 is a graph of AC voltage versus time; and illustrates an output waveform from a drive circuit to a nebuliser.

Referring to FIG. 28, in one application pulsing is achieved by specifying an on-time and off-time for the vibration of the aperture plate. If the on-time is set to 200 vibrations and off-time is set to 200 vibrations, the pulse rate is 50% (½ on ½ off). This means that the flow rate is half of that of a fully driven aperture plate. Any number of vibrations can be specified but to achieve a linear relationship between flow rate and pulse rate a minimum number of on-time vibrations is specified since it takes a finite amount of time for the aperture plate to reach its maximum amplitude of vibrations.

The drive frequency can be started and stopped as required by the microprocessor; this allows control of flow rate by driving the nebuliser for any required pulse rate. The microprocessor can control the on and off times with an accuracy of microseconds.

A nebuliser can be calibrated at a certain pulse rate by measuring how long it takes to deliver a known quantity of solution. There is a linear relationship between the pulse rate and that nebuliser's flow rate. This allows accurate control of the rate of delivery of the aerosolised aqueous solution.

The pulse rate may be lowered so that the velocity of the emerging aerosol is much reduced so that impaction rain-out is reduced.

Another embodiment may have a reduced hole size on the aperture plate which will generate an aerosol with a reduced particle size (<3 um) and at a slower flow rate to provide less 'rain out' in the tubing system.

Detection of when the aperture plate is dry can be achieved by using the fact that a dry aperture plate has a well defined resonant frequency. If the drive frequency is swept from 120 kHz to 145 kHz and the current is measured then if a minimum current is detected less than a set value, the aperture plate must have gone dry. A wet aperture plate has diminished or no resonant frequency. The apparatus of the invention may be configured to determine whether there is any of the first fluid in contact with the aerosol generator 9. By determining an electrical characteristic of the aerosol generator 9, for example the current flowing through the aerosol generator 9, over a range of vibration frequencies, and comparing this electrical characteristic against a pre-defined set of data, it is possible to determine whether the aerosol generator 9 has any solution in contact with the aerosol generator 9. FIG. 29 illustrates a curve 80 of frequency versus current when there is some of the solution in contact with the aerosol generator 9, and illustrates a curve 90 of frequency versus current when there is none of the solution in contact with the aerosol generator 2. FIG. 29 illustrates the wet aperture plate curve 80 and the dry aperture plate curve 90.

If an application requires a constant feed from a drip bag then a pump can be added in line to give fine control of the liquid delivery rate which can be nebulised drip by drip. The rate would be set so that liquid would not build up in the nebuliser. This system is particularly suitable for constant low dose delivery.

The invention is not limited to the embodiments hereinbefore described which may be varied in detail.

The invention claimed is:

1. A fluid delivery system for delivery of fluid from a fluid supply to a patient, the system comprising:
   an aerosol generator including a vibratable member having a plurality of apertures extending between a first surface and a second surface thereof;
   a chamber coupled to the aerosol generator;
   a cylindrical wall extending into the chamber and aligned with a longitudinal axis of the aerosol generator,
   a fluid supply fluidly coupled to the chamber at an inlet port, the inlet port having a central longitudinal axis that is normal to the cylindrical wall and intersects the cylindrical wall; and
   a nasal port fluidly coupled to the chamber.

2. The system of claim 1, wherein the fluid is supplemental oxygen.

3. The system of claim 2, wherein a flow rate of the supplemental oxygen is less than about 3 liters per minute.

4. The system of claim 1, wherein the first surface is configured to receive fluid to be aerosolised.

5. The system of claim 1, wherein the aerosol generator is configured to generate aerosol particles adjacent the second surface.

6. The system of claim 1, wherein the vibratable member is dome-shaped.

7. The system of claim 1, wherein the vibratable member includes a piezoelectric element.

8. The system of claim 1, wherein the nasal port includes a nasal cannula.

9. A fluid delivery system for delivery of fluid from a fluid supply to a patient, the system comprising:
   an aerosol generator including a vibratable member having a plurality of apertures extending between a first surface and a second surface thereof;
   a chamber coupled to the aerosol generator;
   a cylindrical wall extending into the chamber and aligned with a longitudinal axis of the aerosol generator and having a distal opening in the chamber,
   a fluid supply fluidly coupled to the chamber at an inlet port, the inlet port having a central longitudinal axis that extends into the cylindrical wall, the central longitudinal axis intersecting the longitudinal axis of the aerosol generator between the aerosol generator and the distal opening of the cylindrical wall; and
   a nasal port fluidly coupled to the chamber.

10. The system of claim 9, wherein the fluid is supplemental oxygen.

11. The system of claim 10, wherein the vibratable member includes a piezoelectric element.

12. The system of claim 10, wherein the nasal port includes a nasal cannula.

13. The system of claim 10, wherein the aerosol generator is configured to generate aerosol particles, and wherein the aerosol particles contain a therapeutic and/or prophylactic agent.

14. A fluid delivery system for delivery of fluid from a fluid supply to a patient, the system comprising:
   an aerosol generator;
   a chamber coupled to the aerosol generator;
   a cylindrical wall protruding into the chamber and aligned with a longitudinal axis of the aerosol generator,
   an aerosol generator reservoir and interface port located opposite the cylindrical wall, the aerosol generator reservoir extending along a central longitudinal axis angled with respect to the longitudinal axis of the aerosol generator;
   a fluid supply fluidly coupled to the chamber at an inlet port that is normal to the cylindrical wall; and
   a nasal port fluidly coupled to the chamber.

15. The system of claim 14, wherein the fluid is supplemental oxygen.

16. The system of claim 14, wherein the nasal port includes a nasal cannula.

17. The system of claim 14, wherein the aerosol generator includes a vibratable member having a plurality of apertures extending between a first surface and a second surface thereof.

18. The system of claim 17, wherein the vibratable member includes a piezoelectric element.

* * * * *